United States Patent
Matsuda

(10) Patent No.: US 9,129,589 B2
(45) Date of Patent: Sep. 8, 2015

(54) DRIVE APPARATUS, ULTRASONIC PROBE, AND ULTRASONIC DIAGNOSTIC APPARATUS

(71) Applicant: SEIKO EPSON CORPORATION, Tokyo (JP)

(72) Inventor: Hiroshi Matsuda, Gifu (JP)

(73) Assignee: Seiko Epson Corporation, Tokyo (JP)

(*) Notice: Subject to any disclaimer, the term of this patent is extended or adjusted under 35 U.S.C. 154(b) by 190 days.

(21) Appl. No.: 13/904,317

(22) Filed: May 29, 2013

(65) Prior Publication Data

US 2013/0324853 A1 Dec. 5, 2013

(30) Foreign Application Priority Data

May 30, 2012 (JP) ................. 2012-122787

(51) Int. Cl.
*G10K 11/18* (2006.01)
*A61B 8/00* (2006.01)
*G10K 11/34* (2006.01)
*B06B 1/06* (2006.01)
*G01S 7/52* (2006.01)
*G01S 15/89* (2006.01)

(52) U.S. Cl.
CPC .............. *G10K 11/18* (2013.01); *A61B 8/4444* (2013.01); *A61B 8/461* (2013.01); *A61B 8/54* (2013.01); *B06B 1/0629* (2013.01); *G01S 7/5202* (2013.01); *G01S 15/8925* (2013.01); *G10K 11/346* (2013.01)

(58) Field of Classification Search
CPC ........ A61B 8/4444; A61B 8/461; A61B 8/54; B06B 1/0629; G01S 15/8925; G01S 7/5202; G10K 11/18; G10K 11/346

USPC ................... 600/459; 367/135, 137
See application file for complete search history.

(56) References Cited

U.S. PATENT DOCUMENTS

| 2005/0203412 A1 | 9/2005 | Amemiya |
| 2011/0221306 A1 | 9/2011 | Matsuda |
| 2011/0252890 A1 | 10/2011 | Matsuda |
| 2012/0188849 A1 | 7/2012 | Matsuda et al. |

FOREIGN PATENT DOCUMENTS

| EP | 1629778 A1 | 3/2006 |
| JP | 59-025736 A | 2/1984 |
| JP | 59-101141 A | 6/1984 |
| JP | 2005-253699 A | 9/2005 |
| JP | 2005-312587 A | 11/2005 |
| JP | 2006-061252 A | 3/2006 |
| JP | 2011-211164 A | 10/2011 |
| JP | 2011-223490 A | 11/2011 |
| JP | 2012-078934 A | 4/2012 |
| JP | 2012-152319 A | 8/2012 |
| JP | 2012-191497 A | 10/2012 |
| JP | 2012-199389 A | 10/2012 |
| JP | 2013-005250 A | 1/2013 |
| JP | 2013-208164 A | 10/2013 |

*Primary Examiner* — Michael Rozanski
(74) *Attorney, Agent, or Firm* — Global IP Counselors, LLP

(57) ABSTRACT

A drive apparatus for an ultrasonic device includes a transmission circuit for outputting a first through n-th (where n is an integer 2 or greater) drive signal to first through n-th driving electrode line belonging to the ultrasonic device, as well as a control unit for controlling the transmission circuit. In a case where the phase difference between an i-th (where i is an integer 1≤i≤n−1) drive signal and an i+1-th drive signal is a first phase difference, the transmission circuit outputs the first through n-th drive signals at a greater voltage amplitude than a case where the phase difference between the i-th drive signal and the i+1-th drive signal is a second phase difference greater than the first phase difference.

15 Claims, 15 Drawing Sheets

DRIVE APPARATUS, ULTRASONIC PROBE, AND ULTRASONIC DIAGNOSTIC APPARATUS

CROSS-REFERENCE TO RELATED APPLICATIONS

This application claims priority to Japanese Patent Application No. 2012-122787 filed on May 30, 2012. The entire disclosure of Japanese Patent Application No. 2012-122787 is hereby incorporated herein by reference.

BACKGROUND

1. Technical Field

The present invention relates to a drive apparatus, an ultrasonic probe, and an ultrasonic diagnostic apparatus, inter alia.

2. Related Art

One known example of an apparatus for insonifying a subject with ultrasonic waves and receiving reflected waves coming from an interfacial surface at which the acoustic impedance is different within the interior of the subject is an ultrasonic diagnostic apparatus for inspecting the interior of a human body. As an ultrasonic apparatus (ultrasonic probe) to be used in an ultrasonic diagnostic apparatus, Patent Document 1 discloses a technique for scanning a beam in a row direction and in a column direction by arraying piezoelectric elements in a matrix array shape and providing a wiring for every row and column. With this technique, however, the application of a drive signal to the piezoelectric elements creates fluctuations in the electrical potential of a common electrode line, and a problem therefore emerges in that the intensity of ultrasonic waves changes depending on the beam direction (steering angle) in a case where phase scanning is to be carried out.

Japanese Laid-open Patent Publication No. 2006-61252 (Patent Document 1) is an example of the related art.

SUMMARY

Problems to be Solved by the Invention

According to several modes of the invention, it is possible to provide a drive apparatus, ultrasonic probe, and ultrasonic diagnostic apparatus, inter alia, making it possible to reduce changes in ultrasonic wave intensity during phase scanning.

Means Used to Solve the Above-Mentioned Problems

One mode of the invention relates to a drive apparatus for an ultrasonic device, the drive apparatus including a transmission circuit for outputting a first drive signal to an n-th (where n is an integer 2 or greater) drive signal to a first driving electrode line to n-th driving electrode line belonging to the ultrasonic device, as well as a control unit for controlling the transmission circuit; wherein, in a case where the phase difference between an i-th (where i is an integer $1 \le i \le n-1$) drive signal and an i+1-th drive signal from among the first drive signal to n-th drive signal is a first phase difference, the transmission circuit outputs the first drive signal to n-th drive signal at a greater voltage amplitude than a case where the phase difference between the i-th drive signal and the i+1-th drive signal is a second phase difference greater than the first phase difference.

According to one mode of the invention, a smaller phase difference between the i-th drive signal and the i+1-th drive signal correlates to a greater voltage amplitude of the first through n-th drive signals, and thus it is possible to reduce the changes in the intensity of ultrasonic waves in a case where the phase difference is being varied.

In one mode of the invention, the transmission circuit can output the first drive signal to n-th drive signal at a greater voltage amplitude in a case of a frontal emission mode than in a case of a phase scanning mode.

So doing makes it possible to reduce a difference in the ultrasonic wave intensity between the case of the frontal emission mode and the case of the phase scanning mode.

In one mode of the invention, the transmission circuit can have a gain amplifier for which the gain is controlled by the control unit, the control unit controlling the voltage amplitude of the first drive signal to n-th drive signal by controlling the gain of the gain amplifier.

So doing allows the transmission circuit to change the voltage amplitude of the first through n-th drive signals in accordance with the phase difference between the i-th drive signal and the i+1-th drive signal on the basis of the control of the control unit.

In one mode of the invention, the transmission circuit can further include: a signal generation circuit; and a delay circuit for which the delay time is controlled by the control unit; wherein the gain amplifier amplifies a reference signal coming from the signal generation circuit, and the delay circuit generates the first drive signal to n-the drive signal having the phase difference between the i-th drive signal and the i+1-th drive signal by delaying the amplified reference signal on the basis of the control of the control unit.

So doing allows the transmission circuit to output the first through n-th drive signals having a desired phase difference, on the basis of the control of the control unit.

In one mode of the invention, in a case where the first drive signal is outputted at a first timing and the n-th drive signal is outputted at an n-th timing, the gain of the gain amplifier can be increased from the first timing toward a timing intermediate between the first timing and the n-th timing, and reduced from the intermediate timing toward the n-th timing, whereby the voltage amplitude of the first drive signal to n-th drive signal can be increased from the first timing toward the intermediate timing and reduced from the intermediate timing toward the n-th timing.

So doing allows the transmission circuit to output the first through n-th drive signals for which the voltage amplitude increases from the first timing toward the intermediate timing and is reduced from the intermediate timing toward the n-th timing.

In one mode, the transmission circuit can have a voltage selection circuit for selecting one from among a plurality of voltages to serve as a selection voltage, the voltage selection circuit outputting a signal for which the voltage amplitude is the selected selection voltage, the control circuit carrying out a control in which the selection voltage is switched and thereby controlling the voltage amplitude of the signal for which the voltage amplitude is the selection voltage, and the transmission circuit outputting the first drive signal to n-th drive signal on the basis of the signal for which the voltage amplitude is the selection voltage.

So doing allows the transmission circuit to change the voltage amplitude of the first through n-th drive signals in accordance with the phase difference between the i-th drive signal and the i+1-th drive signal on the basis of the control of the control unit.

In one mode of the invention, the transmission circuit can further include: a signal generation circuit; and a delay circuit for which the delay time is controlled by the control unit, wherein the voltage selection circuit delays the signal for which the voltage amplitude is the selection voltage coming from the voltage selection circuit on the basis of the control of the control unit, and the transmission circuit outputs the first drive signal to n-th drive signal having the phase difference between the i-th drive signal and the i+1-th drive signal on the basis of the delayed signal coming from the delay circuit.

So doing allows the transmission circuit to output the first through n-th drive signals having a desired phase difference, on the basis of the control of the control unit.

In one mode of the invention, in a case where the first drive signal is outputted at a first timing and the n-th drive signal is outputted at an n-th timing, the selection voltage of the voltage selection circuit can be increased from the first timing toward a timing intermediate between the first timing and the n-th timing, and reduced from the intermediate timing toward the n-th timing, whereby the voltage amplitude of the first drive signal to n-th drive signal can be increased from the first timing toward the intermediate timing and reduced from the intermediate timing toward the n-th timing.

So doing allows the transmission circuit to output the first through n-th drive signals for which the voltage amplitude increases from the first timing toward the intermediate timing and is reduced from the intermediate timing toward the n-th timing.

One mode of the invention can include a common voltage monitoring circuit for monitoring the voltage of the common electrode line belonging to the ultrasonic device, the control unit controlling the voltage amplitude of the first drive signal to n-th drive signal on the basis of a monitoring result from the common voltage monitoring circuit.

In this case, the transmission circuit is able to change the voltage amplitude of the first through n-th drive signals in accordance with a change in the voltage of the common electrode line.

In one mode of the invention, the control unit can carry out a control in which a greater amplitude of the voltage of the common electrode line correlates to increasing the voltage amplitude of the first drive signal to n-th drive signal, on the basis of the monitoring result from the common voltage monitoring circuit.

In this case, it is possible to reduce changes in the intensity of the ultrasonic waves arising due to changes in the amplitude of the voltage of the common electrode line.

In one mode of the invention, the first drive signal to n-th drive signal can be m (where m is a natural multiple of 0.5) sinusoidal wave(s) or square wave(s).

In this case, it is possible to control the voltage amplitude of the first through n-th drive signals in accordance with the phase difference of the sinusoidal waves or the timing difference of the square waves.

Another mode of the invention relates to an ultrasonic probe including any of the drive apparatuses described above.

Another mode of the invention relates to an ultrasonic diagnostic apparatus including any of the drive apparatuses described above, as well as a display unit for displaying image data for display generated on the basis of a received signal coming from the ultrasonic device.

Another mode of the invention relates to a drive apparatus for an ultrasonic device, the drive apparatus including a transmission circuit for outputting a first pulse signal to n-th (where n is an integer 2 or greater) pulse signal to a first driving electrode line to n-th driving electrode line belonging to the ultrasonic device, as well as a control unit for controlling the transmission circuit; wherein the transmission circuit outputs in a first mode an i-th (where i is an integer $1 \leq i \leq n-1$) pulse signal and an i+1-th signal from among the first pulse signal to n-th pulse signal at an identical timing, and outputs in a second mode the i+1-th pulse signal at a timing that is delayed from the timing at which the i-th pulse signal is outputted, the i-th pulse signal to n-th pulse signal being outputted in the first mode at a greater pulse signal voltage amplitude than in the second mode.

According to the other mode of the invention, the transmission circuit is able to output the first through n-th pulse signals at a greater pulse signal voltage amplitude in the first mode than in the second mode, and thus it is possible to reduce the difference in ultrasonic wave intensity between the case of the first mode and the case of the second mode.

BRIEF DESCRIPTION OF THE DRAWINGS

Referring now to the attached drawings which form a part of this original disclosure.

DETAILED DESCRIPTION OF EXEMPLARY EMBODIMENTS

The following describes in greater detail a preferred embodiment of the invention. The present embodiment described below is not, however, meant to gratuitously limit the content of the invention described in the claims, nor is the entire configuration described in the present embodiment necessarily essential in terms of the solution of the invention.

1. Ultrasonic Elements

Figure 1A:
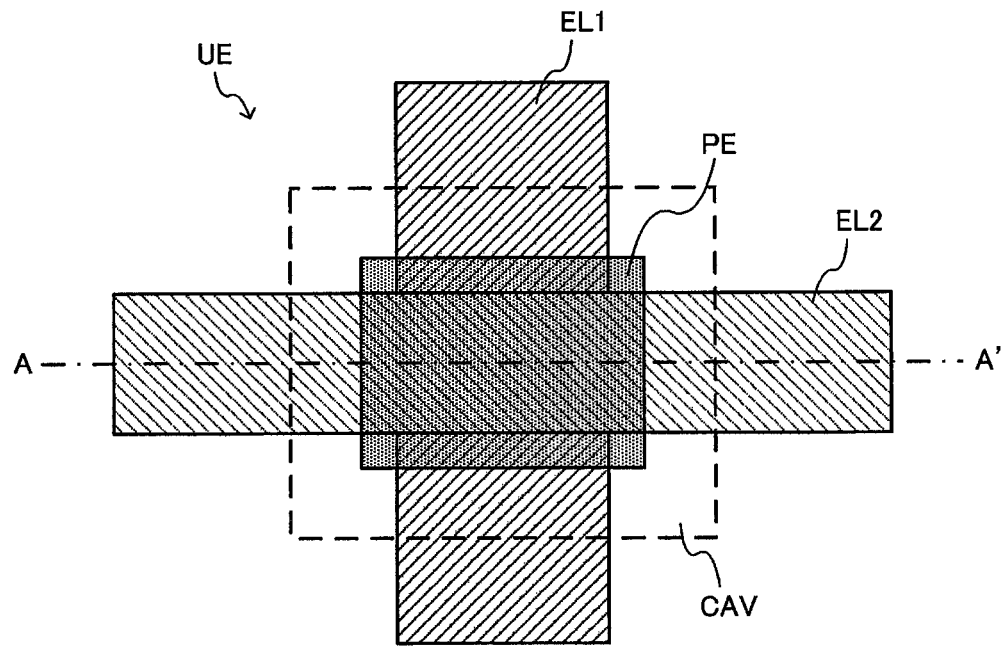
FIGS. 1A and 1B are an example of a basic configuration for an ultrasonic element.
Figure 1B:
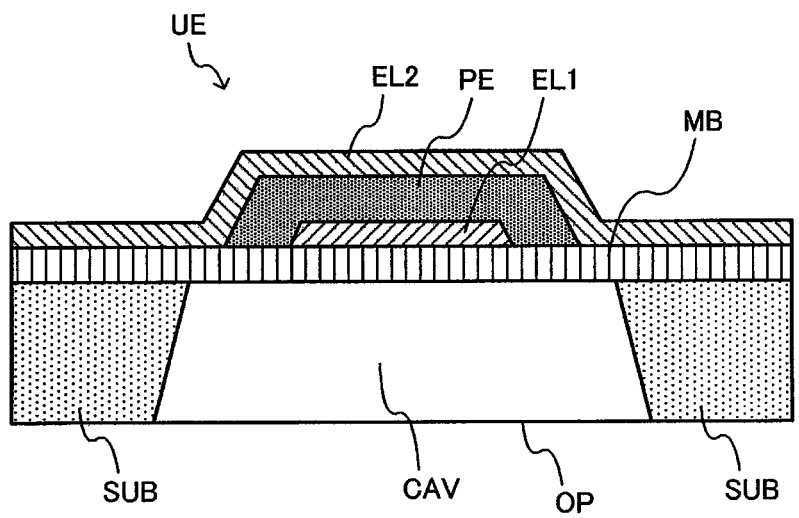

FIGS. 1A and 1B illustrate an example of a basic configuration of an ultrasonic element UE included in an ultrasonic apparatus of the present embodiment. The ultrasonic element UE of the present embodiment has a vibrating film (a membrane or support member) MB and a piezoelectric element part. The piezoelectric element part has a lower electrode (first electrode layer) EL1, a piezoelectric body film (a piezoelectric body layer) PE, and an upper electrode (a second electrode layer) EL2. The ultrasonic element of the present embodiment is not limited to being the configuration of FIG. 1, but rather a variety of modifications can be implemented, such as omitting a part of the constituent elements thereof, replacing same with other constituent elements, or adding other constituent elements.

FIG. 1A is a plan view of the ultrasonic element UE, which is formed on a substrate (a silicon substrate) SUB, the plan view being viewed from a direction perpendicular to the substrate on an element formation surface side. FIG. 1B is a cross-sectional view illustrating a cross-section taken along the A-A' line in FIG. 1A.

The ultrasonic element UE is provided to each opening of a plurality of openings OP arranged in an arrayed shape on the substrate SUB. The ultrasonic elements UE have the vibrating film MB, which closes off the opening OP, and the piezoelectric element part, which is provided atop the vibrating film MB. The piezoelectric element section has: the lower electrode EL1, which is provided atop the vibrating film MB; the piezoelectric body film PE, which is provided so as to at least partially cover the lower electrode EL1; and the upper electrode EL2, which is provided so as to at least partially cover the piezoelectric body film PE.

The first electrode layer EU is formed of, for example, a metal thin film on an upper layer of the vibrating film MB. The first electrode layer EU extends to the outside of an element formation region, as illustrated in FIG. 1A, and can be a wiring that is connected to an adjacent ultrasonic element UE.

The piezoelectric body film PE is formed of, for example, lead zirconate titanate (PZT), and is provided so as to at least partially cover the first electrode layer EL1. The material of the piezoelectric body film PE, however, is not limited to being PZT, but rather, for example, lead titanate (PbTiO3), lead zirconate (PbZrO3), lanthanum lead titanate (Pb, La)TiO3), or the like can be used.

The second electrode layer EL2 is formed of, for example, a metal thin film, and is provided so as to at least partially cover the piezoelectric body film PE. The second electrode layer EL2 extends to the outside of the element formation region, as illustrated in FIG. 1A, and can be a wiring that is connected to an adjacent ultrasonic element UE.

The vibrating film (membrane) MB is provided so as to close off the opening OP with a two-layered structure of, for example, an SiO2 thin film and a ZrO2 thin film. The vibrating film MB supports the piezoelectric body film PE and the first and second electrode layers EL1, EL2, and is also able to vibrate and generate ultrasonic waves according to contraction or expansion of the piezoelectric body film PE.

A cavity region CAV is formed by reactive ion etching (RIE) or the like from a back surface of the silicon substrate SUB (the surface on which the element is not formed). Ultrasonic waves are emitted from the opening OP of the cavity region CAV.

The first electrode (lower electrode) of the ultrasonic elements UE is formed of the first electrode layer EL1, and the second electrode (upper electrode) is formed of the second electrode layer EL2. More specifically, a portion of the first electrode layer EU that is covered by the piezoelectric body film PE forms the first electrode, and a portion of the second electrode layer EL2 that covers the piezoelectric body film PE forms the second electrode. That is, the piezoelectric body film PE is provided sandwiched between the first electrode and the second electrode.

When a voltage is applied between the first electrode and the second electrode, i.e., between the first electrode layer EL1 and the second electrode layer EL2, the piezoelectric body film PE is thereby contracted or extended in the in-plane direction. One of the surfaces of the piezoelectric body film PE is bonded to the vibrating film MB via the first electrode layer EL1, while the second electrode layer EL2 is formed on the other surface, though no other layer is formed atop the second electrode layer EL2. For this reason, the side of the piezoelectric body film PE closer to the vibrating film MB is less readily contracted or expanded, and the side closer to the second electrode layer EL2 is more readily contracted or expanded. As such, when a voltage is applied to the piezoelectric body film PE, a flexure that is convex toward the cavity region CAV is created, causing the vibrating film MB to be flexed. Applying an alternating current voltage to the piezoelectric body film PE causes the vibrating film MB to vibrate with respect to a film thickness direction, and the vibration of the vibrating film MB causes ultrasonic waves to be emitted from the opening OP. The voltage that is applied to the piezoelectric body film PE is, for example, 10 to 30 V, and the frequency is, for example, 1 to 10 MHz.

2. Ultrasonic Device

Figure 2:
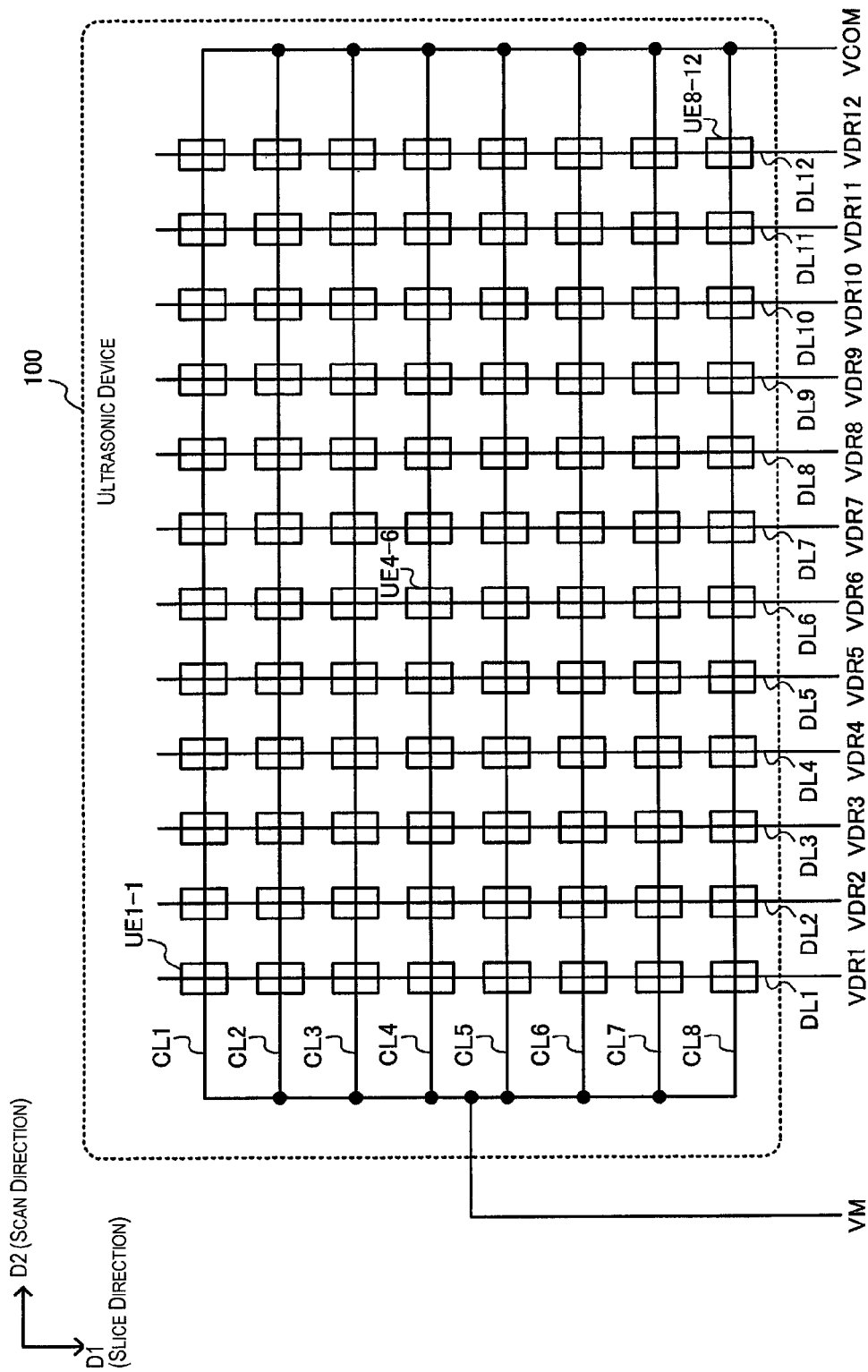
FIG. 2 is an example of a configuration for an ultrasonic device.

FIG. 2 illustrates an example of a configuration for an ultrasonic device 100 of the present embodiment. The ultrasonic device 100 of the present configuration example includes a plurality of the ultrasonic elements UE arranged in an arrayed shape, first through n-th (where n is an integer two or greater) driving electrode lines DL1 to DLn, and first through m-th (where m is an integer two or greater) common electrode lines CL1 to CLm. FIG. 2 illustrates a case where m=8 and n=12, by way of example, but other values can be used. The ultrasonic device 100 of the present embodiment is, however, not limited to being the configuration of FIG. 2, but rather a variety of modifications can be implemented, such as omitting a part of the constituent elements thereof, replacing same with other constituent elements, or adding other constituent elements.

The plurality of ultrasonic elements UE are arranged in a matrix shape with m rows and n columns. As illustrated in, for example, FIG. 2, the ultrasonic elements are arranged in eight rows along a first direction D1 and 12 columns along a second direction D2 that intersects with the first direction D1.

The ultrasonic elements UE can adopt, for example, the configurations illustrated in FIGS. 1A and 2B. In the description that follows, in a case where the position of an ultrasonic element UE within the array is to be specified, then, for example, an ultrasonic element positioned in the fourth row and the sixth column would be denoted by UE4-6. For example, eight ultrasonic elements UE1-6, UE2-6, . . . , UE7-6, UE8-6 are arranged in the sixth column. As another example, 12 ultrasonic elements UE4-1, UE4-2, . . . , UE4-11, UE4-12 are arranged in the fourth row.

The first through twelfth (more broadly, n-th) driving electrode lines DL1 to DL12 are wired along the first direction D1. Of the first through twelfth driving electrode lines DL1 to DL12, the j-th (where j is an integer 1≤j≤12) driving electrode line DLj is connected to the first electrode belonging to each of the ultrasonic elements UE arranged in the j-th column.

During a transmission period for issuing forth ultrasonic waves, a first through twelfth drive signal VDR1 to VDR12 outputted by a drive device 200 (description to follow) is supplied to respective ultrasonic elements via the driving electrode lines DL1 to DL12. During a receiving period for receiving an ultrasonic wave echo signal, a received signal coming from the ultrasonic elements UE is outputted via the driving electrode lines DL1 to DL12. A more detailed description of the drive signals VDR1 to VDR12 is to follow.

The first through eighth (more broadly, m-th) common electrode lines CL1 to CL8 are wired along the second direction D2. The second electrodes belonging to the ultrasonic elements UE are connected to any of the first through m-th common electrode lines CL1 to CLm. More specifically, as illustrated in, for example, FIG. 2, an i-th (where i is an integer $1 \leq i \leq 8$) common electrode line CLi of the first through eighth common electrode lines CL1 to CL8 is connected to the second electrodes belonging to the ultrasonic electrodes UE arranged in the i-th column.

A common voltage VCOM is supplied to the first through eighth common electrode lines CL1 to CL8. The common voltage should be a constant direct current voltage, and need not be 0 V, i.e., the ground potential.

For example, as regards the ultrasonic element UE1-1 illustrated in FIG. 2, the first electrode is connected to the driving electrode line DL1, and the second electrode is connected to the first common electrode line CL1. Also, as regards the ultrasonic element UE4-6 illustrated in FIG. 2, the first electrode is connected to the sixth driving electrode line DL6, and the second electrode is connected to the fourth common electrode line CL4.

It would be possible to provide a voltage monitoring wiring for monitoring a voltage VM of the common electrode lines CL1 to CL8 of the first through eighth (more broadly, m-th) common electrode lines CL1 to CL8. So doing would make it possible to monitor the voltage of the common electrode lines CL1 to CL8 using a common voltage monitoring circuit 250 (description to follow).

The arrangement of the ultrasonic elements UE, however, is not limited to being the matrix arrangement of m rows and n columns illustrated in FIG. 2. For example, the configuration can be a so-called staggered arrangement in which m ultrasonic elements are arranged in odd-numbered ultrasonic element columns, and m−1 ultrasonic elements are arranged in even-numbered ultrasonic element columns.

A voltage of the difference between the drive signal voltage and the common voltage is applied to each of the ultrasonic elements UE, and ultrasonic waves of a predetermined frequency are emitted. For example, a difference VDR1−VCOM between the drive signal voltage VDR1 supplied to the driving electrode line DL1 and the common voltage VCOM supplied to the common electrode line CL1 is applied to the ultrasonic element UE1-1 in FIG. 2. Similarly, a difference VDR6−VCOM between the drive signal voltage VDR6 supplied to the driving electrode line DL6 and the common voltage VCOM supplied to the common electrode line CL4 is applied to the ultrasonic element UE4-6.

In a case where the phases of the first through twelfth drive signals VDR1 to VDR12 are matched to each other, the ultrasonic waves that are emitted from each of the ultrasonic elements are composited together, and ultrasonic waves emitted in a direction perpendicular to the element array plate of the ultrasonic device 100 (the normal direction of the array plane) are formed. In a case where the drive signals VDR1 to VDR12 have a phase difference from each other, however, then the composited ultrasonic waves are emitted in a direction shifted away from the normal direction of the array plane in accordance with the phase difference. When this phenomenon is made use of, it is possible to change the emission direction of the ultrasonic waves by changing the phase difference of the drive signals. Scanning the emission direction (beam direction) of the ultrasonic waves by controlling the phase difference of the drive signals is called "phase scanning" or "beam steering".

Figure 3:
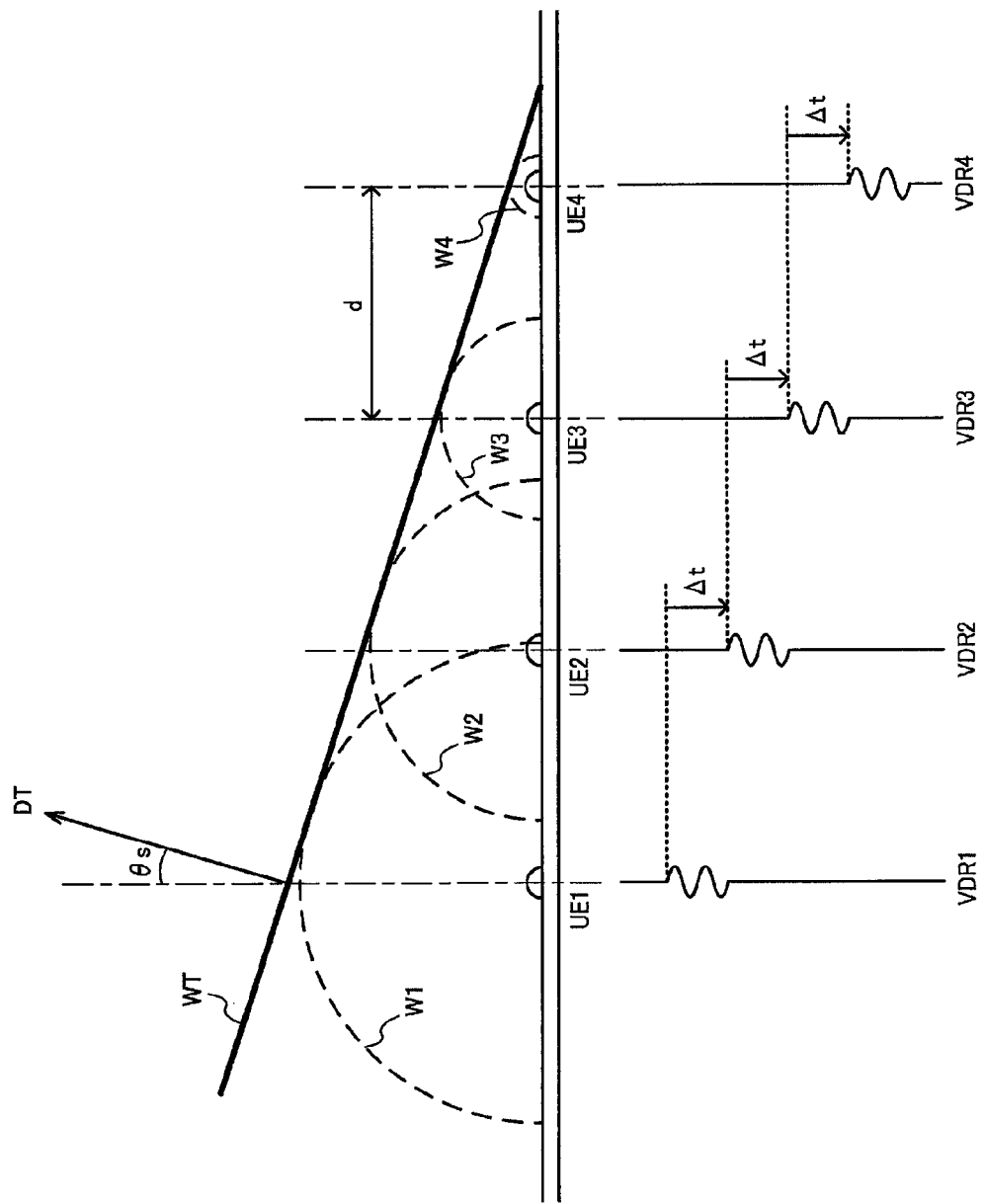
FIG. 3 is a drawing for describing phase scanning in an ultrasonic device.

FIG. 3 is a drawing for describing the phase scanning in the ultrasonic device 100 of the present embodiment. For the sake of simplicity, FIG. 3 describes four ultrasonic elements UE1 to UE4. The ultrasonic elements UE1 to UE4 are arranged at equal intervals d. The drive signals VDR1 to VDR4 supplied thereto are phased so that the drive signal VDR1 is earliest, and the drive signals VDR2, VDR3, and VDR4 are delayed in the stated order by a predetermined phase difference. That is, the drive signals VDR1 to VDR4 are supplied in association with a predetermined time difference $\Delta t$ in the stated order VDR1, VDR2, VDR3, and VDR4.

FIG. 3 illustrates wavefronts W1 to W4 at a given time of the ultrasonic waves emitted from the ultrasonic elements UE1 to UE4. The ultrasonic waves emitted from the ultrasonic elements are composited together to form a wavefront WT of the composited ultrasonic waves. A normal direction DT of the wavefront WT serves as the emission direction (beam direction) of the composited ultrasonic waves. An angle θs formed by the beam direction DT and the normal direction of the array plane is given by:

$$\sin \theta x = c \times \Delta t / d \qquad (1)$$

Herein, c, $\Delta t$, and d are the speed of sound, the time difference of the drive signals, and the element spacing, respectively.

This manner of phase scanning, i.e., changing the phase difference (time difference) of the drive signals supplied to the ultrasonic elements makes it possible to change the beam direction. More specifically, in, for example, the configuration example illustrated in FIG. 2, changing the phase difference (time difference) of the drive signals VDR1 to VDR12 supplied to the driving electrode lines DL1 to DL12 makes it possible to scan the beam direction along a second direction D2. Namely, the second direction D2 is a scan direction for phase scanning, and the first direction D1 is a slice direction.

Figure 4A:
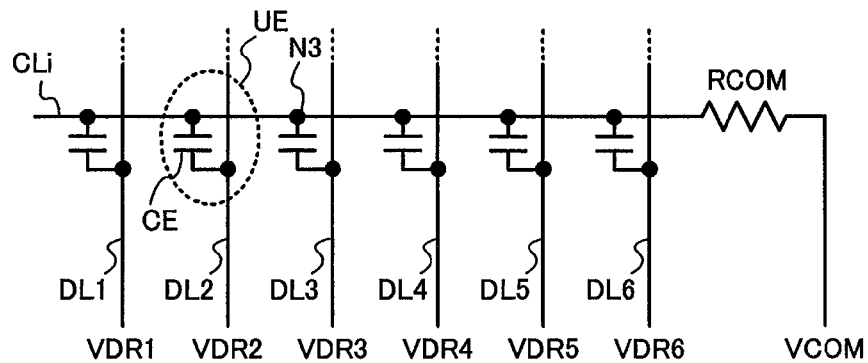
FIGS. 4A, 4B, and 4C are drawings for describing a change in the electrical potential of a common electrode line during phase scanning.
Figure 4B:
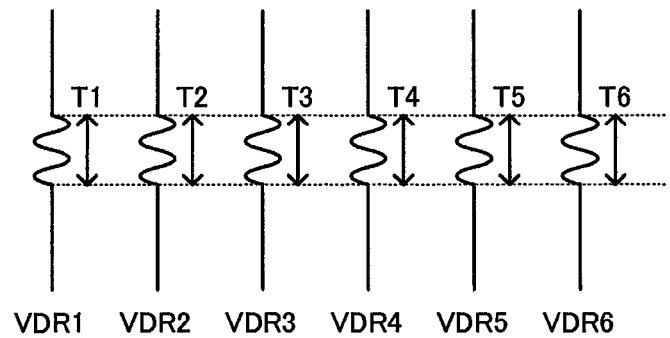
Figure 4C:
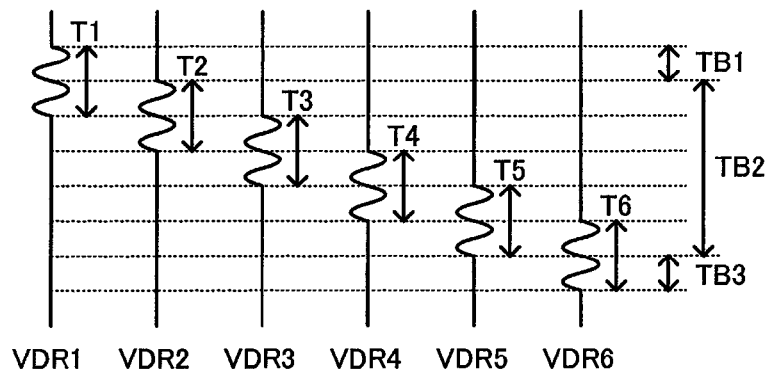

FIGS. 4A, 4B, and 4C are drawings for describing the changes in electrical potential for the common electrode lines CL1 to CL8 during phase scanning. For the sake of simplicity, the description shall relate to the six ultrasonic elements UE and driving electrode lines DL1 to DL6 of the i-th row and the i-th common electrode line CLi.

FIG. 4A illustrates an equivalent circuit of the common electrode line CLi and the ultrasonic elements UE. Electrically, the ultrasonic elements UE can be regarded as capacitative elements (capacitors) CE. The common electrode line CLi has a wiring resistance RCOM, and thus the common voltage VCOM is applied to the ultrasonic elements UE via a resistor element RCOM. The common electrode line CLi is connected to the driving electrode lines DL1 to DL6 via the capacitances CE belonging to the ultrasonic elements UE, and thus the drive signals VDR1 to VDR6 inputted to the driving electrode lines DL1 to DL6 cause the electrical potential of the common electrode line CLi to change.

FIG. 4B illustrates one example of waveforms of the drive signals VDR1 to VDR6 in frontal emission, i.e., a case where the beam direction of the ultrasonic waves is the normal direction of the array plane (a first mode or frontal emission mode). During frontal emission, drive signals of the same phase are inputted at the same timing, and thus the six ultrasonic elements are driven at the same time. That is, the drive signals VDR1 to VDR6 are inputted at first through sixth times T1 to T6, and the overlapping degree of the first through sixth times T1 to T6 is 6.

FIG. 4C illustrates one example of waveforms of the drive signals VDR1 to VDR6 in a case where the beam direction of the ultrasonic waves is a direction that has been shifted from the normal direction of the array plane (a second mode or phase scanning mode). In such a case, the drive signals are inputted accompanied by a phase difference (time difference) from each other. At times TB1, TB3, there is one ultrasonic element that is driven at the same time, while at a time TB2 there are two ultrasonic elements that are driven at the same time. That is, the drive signals VDR1 to VDR6 are inputted at the first through sixth times T1 to T6, and at the times TB1, TB3, the overlapping degree is 1, while at the time TB2 the overlapping degree is 2.

In this manner, in the case of the front emission mode illustrated in FIG. 4B, all of the ultrasonic elements connected to a single common electrode line are driven at the same time, and thus there are considerable changes in the electrical potential (voltage fluctuations) of the common electrode line. In the case of the phase scanning mode illustrated in FIG. 4C, however, fewer ultrasonic elements are driven at the same time, and thus the changes in electrical potential (voltage fluctuations) of the common electrode line are smaller than the case of FIG. 4B. The description above relates to a single common electrode line, but the same is also true of a case where there are a plurality of the common electrode lines.

FIGS. 5A, 5B, 6A, and 6B illustrate one example of drive signal waveforms and also of voltage fluctuations of the common electrode line, given by circuit simulation. More specifically, the drive signal waveform is the waveform of the drive signal VDR3 in FIG. 4A, and the voltage of the common electrode line is a voltage V(N3) of a common electrode node (N3 in FIG. 4A) of an ultrasonic element into which the drive signal VDR3 is inputted.

Figure 5A:
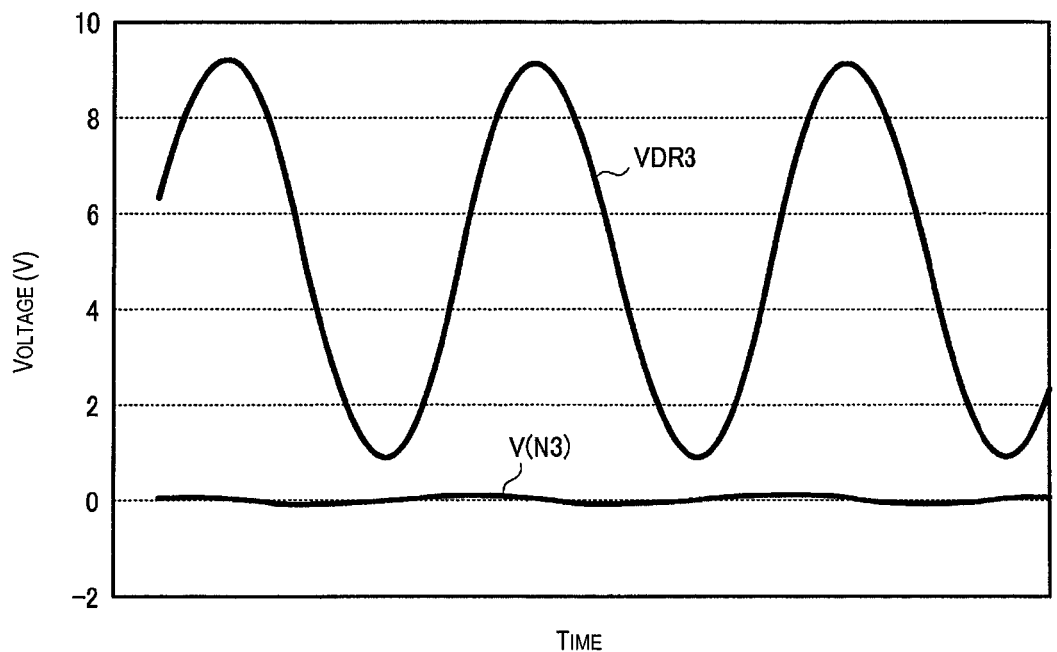
FIGS. 5A and 5B are one example of voltage fluctuations of a common electrode line and a drive signal waveform.
Figure 5B:
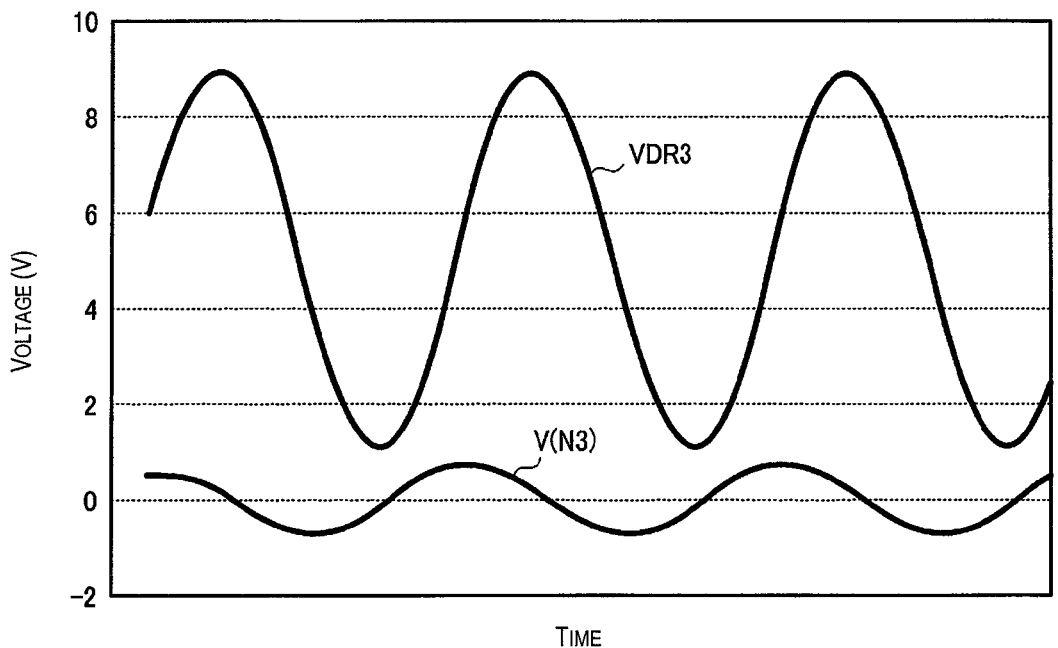

FIG. 5A illustrates the case of a first steering angle (the angle formed by the beam direction and the normal direction of the array plane) θ1; FIG. 5B illustrates the case of a second steering angle θ2 (<θ1); and FIG. 6A illustrates the case of frontal emission (where the steering angle is 0).

Figure 6A:
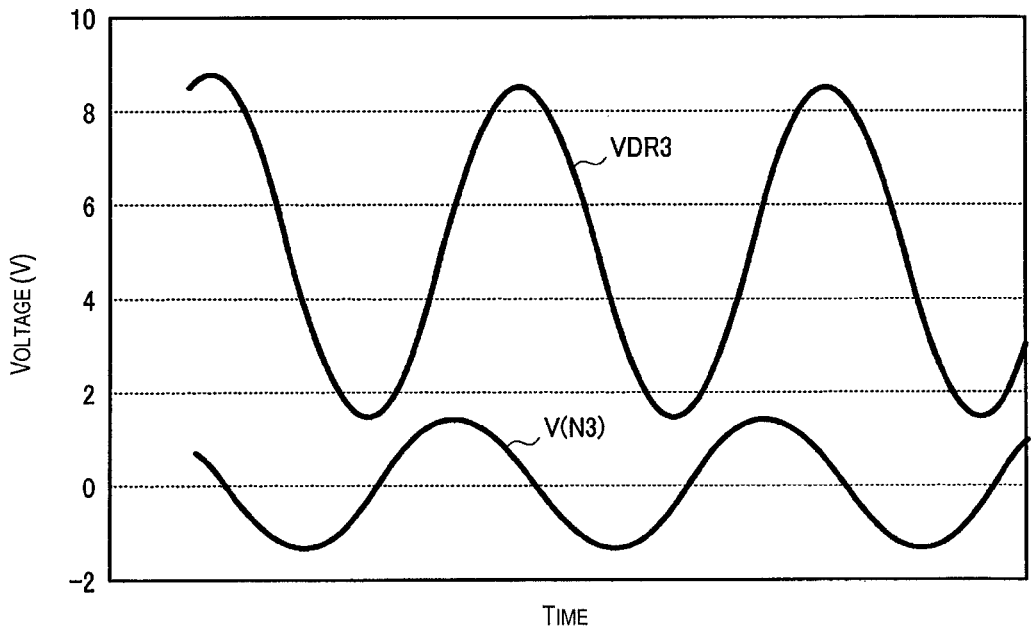
FIGS. 6A and 6B are one example of voltage fluctuations of a common electrode line and a drive signal waveform.

As will be understood from FIGS. 5A, 5B, and 6A, a smaller steering angle, i.e., a smaller phase difference (time difference) in the drive signals correlates to greater voltage fluctuations in the common electrode line. This is because, as stated above, a smaller phase difference (time difference) in the drive signals correlates to a greater number of ultrasonic elements being driven at the same time, and, conversely, a greater phase difference (time difference) in the drive signals correlates to a lesser number of ultrasonic elements being driven at the same time.

Figure 6B:
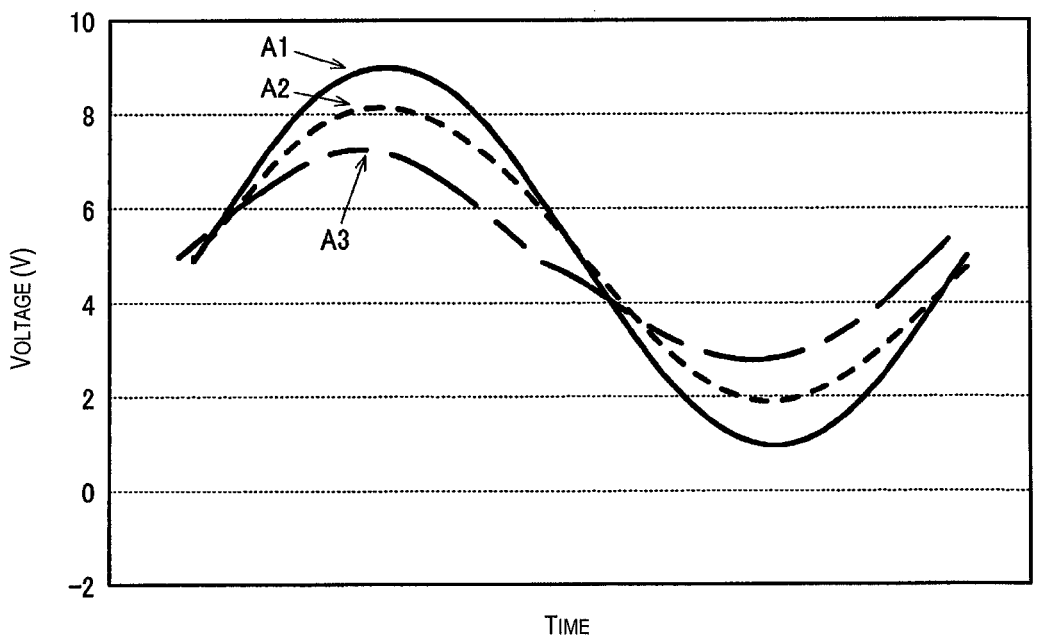

FIG. 6B illustrates a voltage (effective voltage) VDR3–V(N3) applied to the ultrasonic elements. In a case where the steering angle is θ1, the amplitude of the effective voltage becomes the largest, as illustrated by A1. In the case of the steering angle θ2 (<θ1), the amplitude of the effective voltage becomes smaller than that of the case of the steering angle θ1, as illustrated by A2, while in the case of frontal emission the amplitude of the effective voltage becomes the smallest, as illustrated by A3. In this manner, a smaller steering angle, i.e., a smaller phase difference (time difference) in the drive signals correlates to a smaller amplitude of the effective voltage, and, conversely, a greater steering angle, i.e., a greater phase difference (time difference) in the drive signals correlates to a greater amplitude of the effective voltage.

Should the amplitude of the effective voltage be changed depending on the steering angle, the intensity of the ultrasonic waves being emitted would be changed depending on the steering angle. For example, in the case of phase scanning with an ultrasonic diagnostic apparatus, the ultrasonic wave intensity being emitted changes depending on the beam direction, and thus the intensity of the echo signal also changes depending on the direction. As a result, problems emerge such as in that it is difficult to obtain an accurate echo image.

A drive apparatus 200 of the present embodiment is intended to provide a means for resolving this problem. According to the drive apparatus 200 of the present embodiment, it is possible to change the voltage amplitude of the drive signals in accordance with the phase difference (time difference) in the first through n-th drive signals VDR1 to VDRn. So doing makes it possible to reduce changes in the ultrasonic intensity corresponding to the steering angle, or alternatively to have a substantially constant intensity, during the phase scanning mode.

The drive apparatus 200 of the present embodiment can also be applied to a bulk ultrasonic element (an ultrasonic element using a bulk vibrator), but is applied by driving thin-film ultrasonic elements such as are illustrated in FIGS. 1A and 1B. This is because with a thin-film ultrasonic element, the capacitance CE illustrated in FIG. 4A would be larger than with a bulk ultrasonic element, and therefore the changes in electrical potential of the common electrode line would be larger.

3. Drive Apparatus

Figure 7:
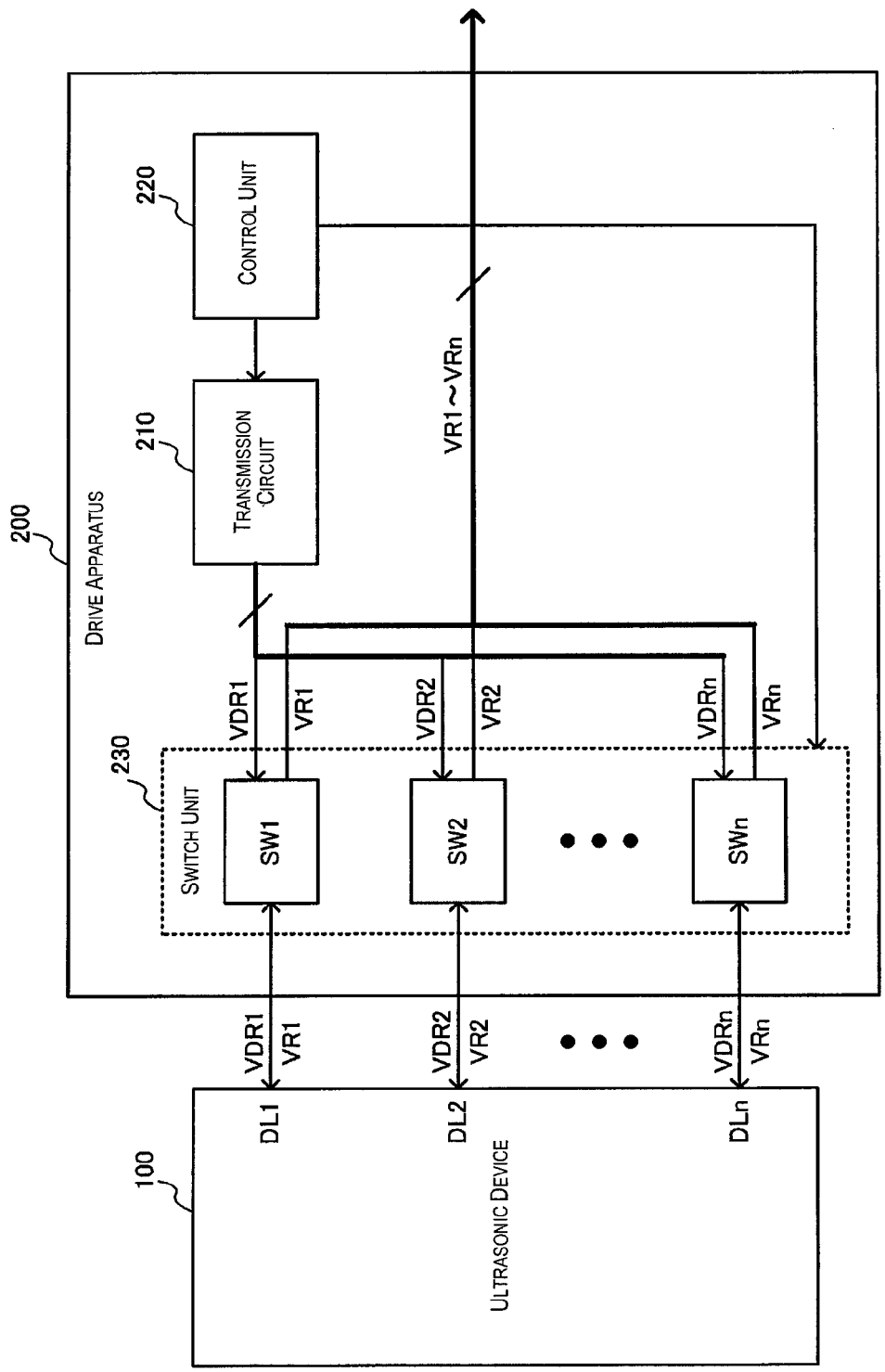
FIG. 7 is a first configuration example for a drive apparatus.

FIG. 7 illustrates a first configuration example of the drive apparatus 200 of the present embodiment. The drive apparatus 200 of the first configuration example is a drive apparatus for the ultrasonic device 100, and includes a transmission circuit 210, a control unit 220, and a switch unit 230. The drive apparatus 200 of the present embodiment is not limited to being the configuration of FIG. 7, but rather a variety of modifications can be implemented, such as omitting a part of the constituent elements thereof, replacing same with other constituent elements, or adding other constituent elements.

The transmission circuit 210 outputs the first through n-th drive signals VDR1 to VDRn to the first through n-th (where n is an integer 2 or greater) driving electrode lines DL1 to DLn belonging to the ultrasonic device 100. A description of the configuration of the transmission circuit 210 is to follow.

The control unit 220 controls the transmission circuit 210 and the switch unit 230. More specifically, the control unit 220 controls the voltage amplitude and phase difference (timing) of the drive signals VDR1 to VDRn outputted by the transmission circuit 210. The control unit 220 also controls switching between a drive signal and a received signal, which is carried out by the switch unit 230.

The switch unit 230 includes switch circuits SW1 to SWn, and carries out switching between a drive signal and a received signal. For example, the switch circuit SW1 outputs the drive signal VDR1, coming from the transmission circuit 210, to the driving electrode line DL1 of the ultrasonic device 100 during a transmission period, and outputs a received signal, coming from the driving electrode line DL1, to a receiver unit 240 (not shown) during a reception period.

In a case where the phase difference between an i-th (where i is an integer 1≤i≤n−1) drive signal VDRi and an i+1-th drive signal VDRi+1 of the first through n-th drive signals VDR1 to VDRn is a first phase difference, the transmission circuit 210 outputs the first through n-th drive signals VDR1 to VDRn at a greater voltage amplitude than that of a case where the phase difference between the i-th drive signal VDRi and the i+1-th drive signal VDRi+1 is a second phase difference greater than the first phase difference.

So doing makes it possible to having an increasingly greater voltage amplitude of the drive signals VDR1 to VDRn with an increasingly smaller phase difference between the drive signals VDRi and VDRi+1, and thus makes it possible to minimize a drop in voltage (effective voltage) applied to the ultrasonic elements in a case where the phase difference is small. As a result, it is possible to reduce the difference in ultrasonic wave intensity arising due to a variance in the phase difference between drive signals (a variance in the steering angle).

In the case of the frontal emission mode, the transmission circuit 210 outputs the first through n-th drive signals VDR1 to VDRn at a greater voltage amplitude than that of the case of the phase scanning mode. So doing makes it possible to increase the voltage amplitude of the drive signals VDR1 to VDRn in the case of the frontal emission mode, and thus makes it possible to reduce the difference in voltages (effective voltages) applied to the ultrasonic elements between the case of the frontal emission mode and the case of the phase scanning mode. As a result, it is possible to reduce the difference in ultrasonic wave intensity arising between the case of the frontal emission mode and the case of the phase scanning mode.

Though the foregoing description describes a sinusoidal signal by way of example as the drive signals VDR1 to VDRn, the drive signals are not limited to being sinusoidal. For example, a square-wave pulse signal can be used. For example, the transmission circuit 210 would output at the same timing an i-th (where i is an integer 1≤i≤n−1) pulse signal and an i+1-th pulse signal from among first through n-th pulse signals during a first mode (the frontal emission mode). During a second mode (the phase scanning mode), the i+1-th pulse signal would be outputted at a timing that is delayed from the timing at which the i-th pulse signal is outputted.

Figure 8A:
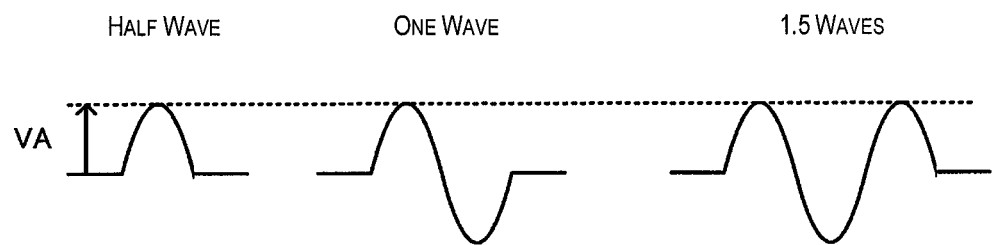
FIGS. 8A and 8B are examples of a signal waveform of a drive signal.
Figure 8B:
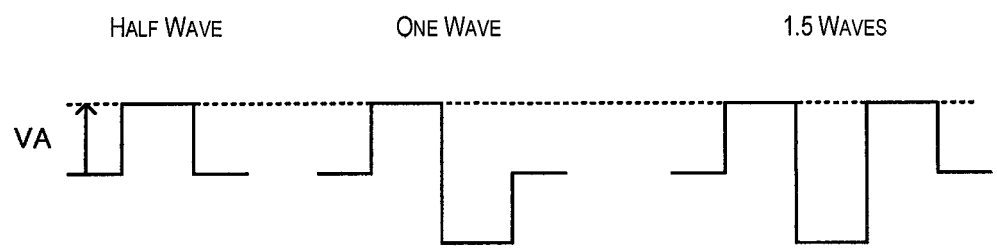

FIGS. 8A and 8B illustrate examples of the signal waveforms of the drive signals. FIG. 8A is a sinusoidal drive signal, and illustrates by way of example half of a sinusoidal wave, one full sinusoidal wave, and 1.5 sinusoidal waves. FIG. 8B is a square-wave drive signal, and illustrates by way of example half of a square wave, one full square wave, and 1.5 square waves. "VA" is indicative of the voltage amplitude of each of the signals.

It is thus possible to use k (where k is a natural multiple of 0.5, i.e., k=0.5, 1, 1.5, 2, . . . ) sinusoidal waves or square waves as the drive signals VDR1 to VDRn.

The changes in the amplitude of the effective voltage arising due to the steering angle described in FIGS. 4A to 4C, 5A and 5B, and 6A and 6B take place in the same manner in a case where the drive signals are square waves, as well. Namely, a smaller steering angle, i.e., a smaller timing difference in the drive signals correlates to a smaller amplitude of the effective voltage, and, conversely, a greater steering angle, i.e., a greater timing difference in the drive signals correlates to a greater amplitude of the effective voltage.

Similarly with respect to the case of a sinusoidal wave, outputting in the first mode (the frontal emission mode) the first through n-th pulse signals of a greater pulse signal voltage amplitude than that of the second mode (the phase scanning mode) allows the transmission circuit 210 to reduce the difference in the effective voltage between the case of the frontal emission mode and the case of the phase scanning mode.

Figure 9:
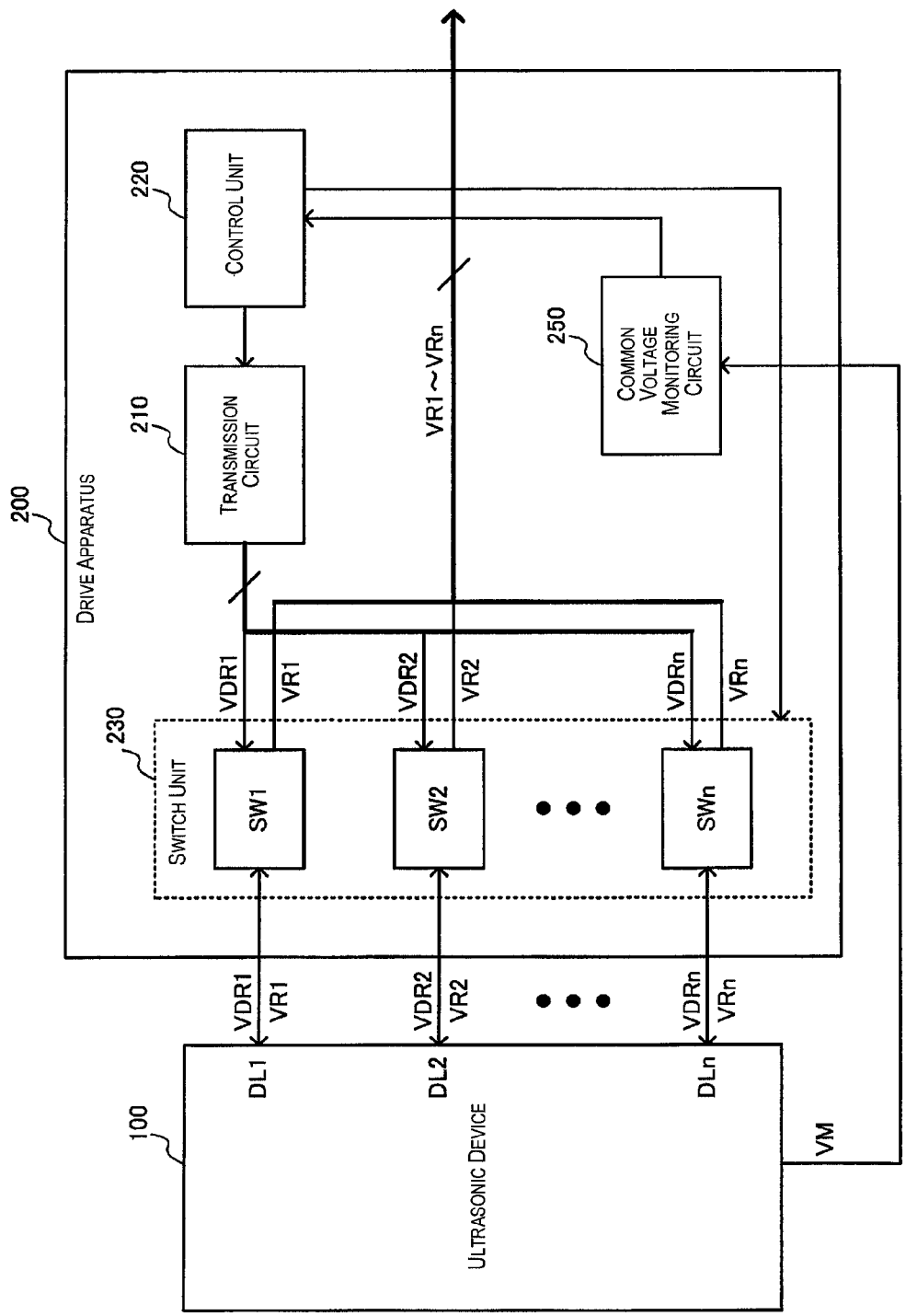
FIG. 9 is a second configuration example for a drive apparatus.

FIG. 9 illustrates a second configuration example of the drive apparatus 200 of the present embodiment. The drive apparatus 200 of the second configuration example is a drive apparatus for the ultrasonic device 100, and includes a transmission circuit 210, a control unit 220, a switch unit 230, and a common voltage monitoring circuit 250. The drive apparatus 200 of the present embodiment is not limited to being the configuration of FIG. 9, but rather a variety of modifications can be implemented, such as omitting a part of the constituent elements thereof, replacing same with other constituent elements, or adding other constituent elements.

The transmission circuit 210 and the switch unit 230 are the same as those of the first configuration example (FIG. 7), which has already been described, and thus a more detailed description thereof has been omitted herein.

The common voltage monitoring circuit 250 monitors the voltage VM of the common electrode lines CL1 to CL8 belonging to the ultrasonic device 100.

The control unit 220, similarly with respect to the first configuration example, controls the transmission circuit 210 and the switch unit 230. In particular, in the second configuration example, the voltage amplitude of the first through n-th drive signals VDR1 to VDRn is controlled on the basis of a monitoring result of the common voltage monitoring circuit 250.

Figure 10:
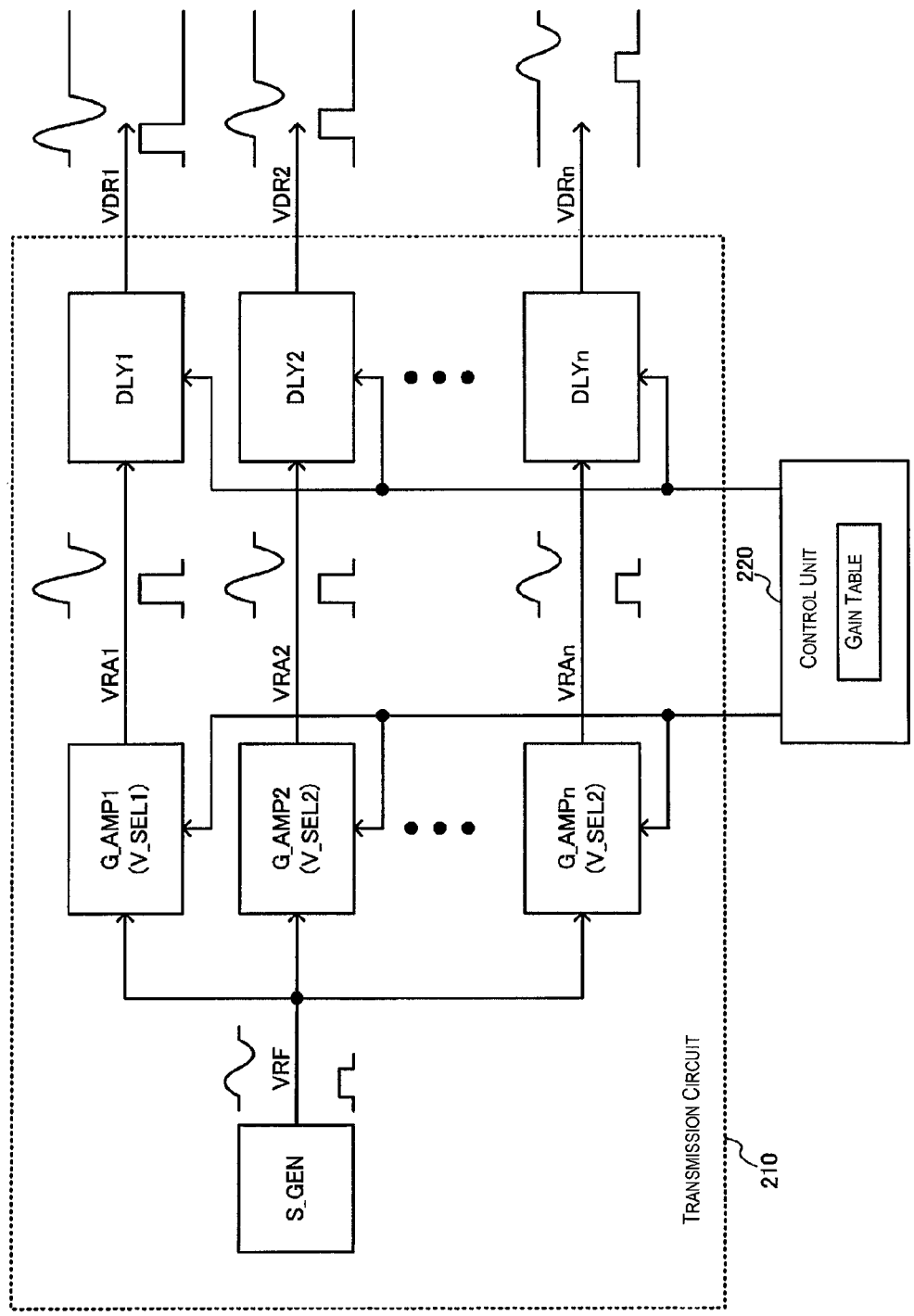
FIG. 10 is one example of control in the first configuration example of the drive apparatus, as well as a configuration example for a transmission circuit.

FIG. 10 illustrates one example of the control in the configuration example of the transmission circuit 210 and the first configuration example of the drive apparatus 200. The transmission circuit 210 includes a signal generation circuit S_GEN, gain amplifiers G_AMP1 to G_AMPn (or voltage selection circuits VSEL1 to VSELn), and delay circuits DLY1 to DLYn. The transmission circuit 210 of the present embodiment is not limited to being the configuration of FIG. 10, but rather a variety of modifications can be implemented, such as omitting a part of the constituent elements thereof, replacing same with other constituent elements, or adding other constituent elements.

The signal generation circuit S_GEN outputs a reference signal VRF. The reference signal VRF can be a sinusoidal wave, or can be a square wave.

With the gain amplifiers G_AMP1 to G_AMPn, gain is controlled by the control unit 220. The gain amplifiers G_AMP1 to G_AMPn amplify the reference signal VRF by the gain that has been set by the control unit 220, and output amplified reference signals VRA1 to VRAn. That is, controlling the gain of the gain amplifiers G_AMP1 to G_AMPn allows the control unit 220 to control the voltage amplitude of the first through n-th drive signals VDR1 to VDRn.

With the delay circuits DLY1 to DLYn, the delay time is controlled by the control unit 220. By delaying the amplified reference signals VRA1 to VRAn on the basis of the control of the control unit 220, the delayed circuits DLY1 to DLYn generate first through n-th drive signals VDR1 to VDRn having a desired phase difference (timing difference). That is, first through n-th drive signals VDR1 to VDRn having a phase difference between the i-th (where i is an integer 1≤i≤n−1) drive signal VDRi and the i+1-th drive signal VDRi+1 are generated.

The gain amplifiers G_AMP1 to G_AMPn can be replaced by the voltage selection circuits V_SEL1 to V_SELn. The voltage selection circuits V_SEL1 to V_SELn select one of a plurality of voltages to serve as a selection voltage on the basis of the control of the control unit 220. Then, in synchronization with the reference signal VRF coming from the signal generation circuit S_GEN, signals VRA1 to VRAn for which the voltage amplitude is the selection voltage are outputted. That is, carrying out a control for switching the selection voltage allows the control unit 220 to control the voltage amplitude of the first through n-th drive signals VDR1 to VDRn.

By delaying the signals VRA1 to VRAn for which the voltage amplitude is the selection voltage coming from the voltage selection circuits V_SEL1 to V_SELn on the basis of the control unit 220, the delay circuits DLY1 to DLYn generate the first through n-th drive signals VDR1 to VDRn having a desired phase difference (timing difference). That is, the first through n-th drive signals VDR1 to VDRn having a phase difference between the i-th (where i is an integer 1≤i≤n−1) drive signal VDRi and the i+1-th drive signal VDRi+1 are generated.

The control unit 220 has a register (storage circuit) in which a gain table is stored, and is able to set the gain of the gain amplifiers G_AMP1 to G_AMPn on the basis of the gain table. The gain table can be, for example, a table indicative of a relationship between the steering angle and the gain, or can be a table indicative of a relationship between the phase difference (timing difference) and the gain.

Further, in the configuration in which the voltage selection circuits V_SEL1 to V_SELn are used, instead of the gain table, a table indicative of, for example a relationship between the steering angle and the selection voltage can be used, or a table indicative of a relationship between the phase difference (timing difference) and the selection voltage can be used.

Figure 11:
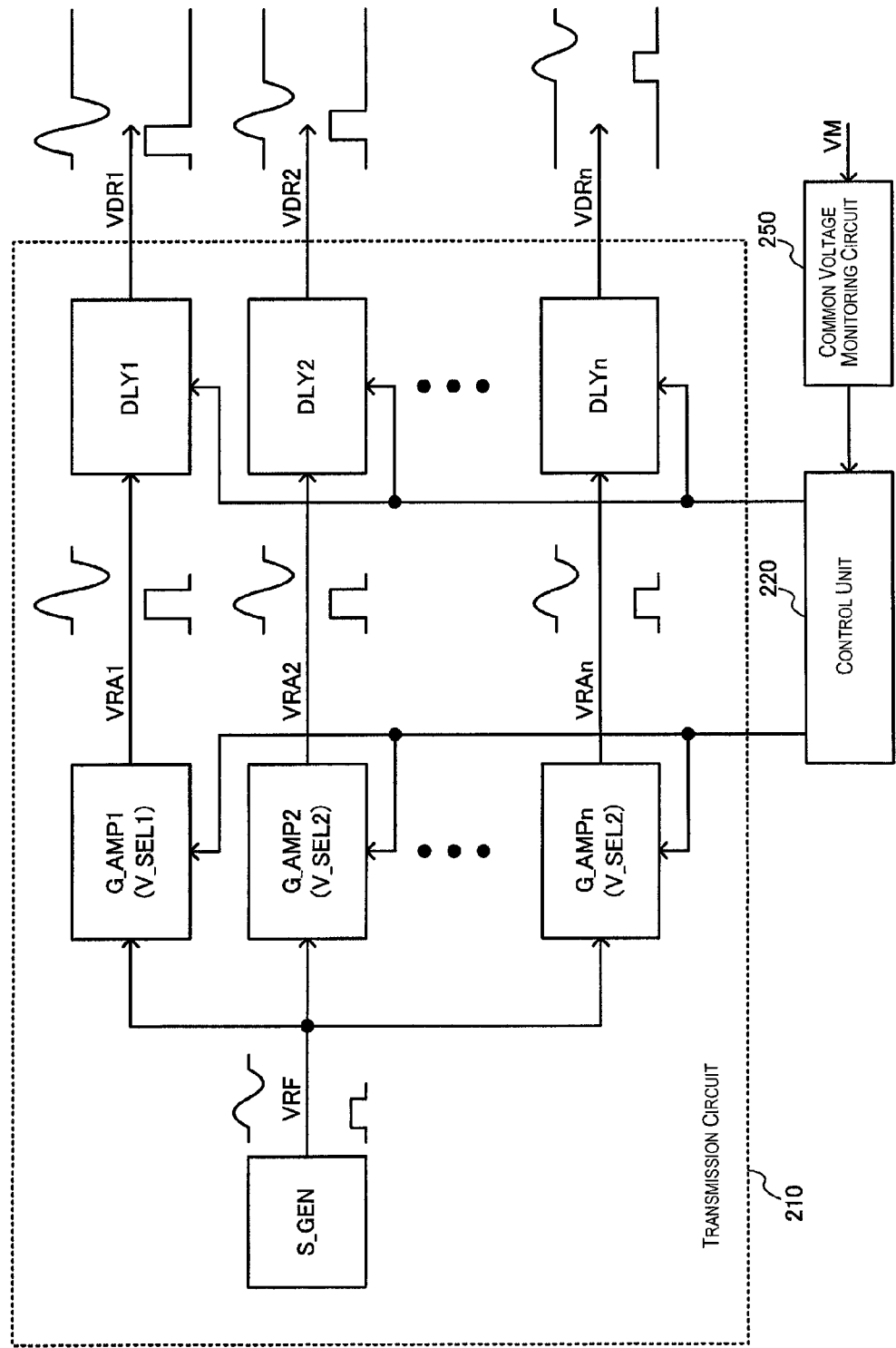
FIG. 11 is one example of control in the second configuration example of the drive apparatus, as well as a configuration example for a transmission circuit.

FIG. 11 illustrates one example of the control in the configuration example of the transmission circuit 210 and the second configuration example of the drive apparatus 200. The transmission circuit 210 is the same as the configuration illustrated in FIG. 10, and thus a more detailed description thereof has been omitted herein.

The control unit 220 controls the voltage amplitude of the first through n-th drive signals VDR1 to VDRn on the basis of the monitoring result of the common voltage monitoring circuit 250. More specifically, the control unit 220 carries out a control in which a greater amplitude of the voltage VM of the common electrode line correlates to a greater voltage amplitude of the drive signals VDR1 to VDRn. So doing makes it possible to minimize changes in the effective voltage, and thus makes it possible to reduce the difference in ultrasonic wave intensity arising due to a variance in the phase difference (timing difference) of the drive signals during the phase scanning mode. It is also possible to reduce the difference in ultrasonic wave intensity between the frontal emission mode and the phase scanning mode.

FIGS. 12A to 12D illustrate a first example of gain control by the control unit 220. The description herein relates to the first through third drive signals VDR1 to VDR3, for the sake of simplicity. The control unit 220 sets the gain to 1, 2, or 3, in accordance with the overlapping degree of the drive signals. FIGS. 12A to 12D illustrates sinusoidal drive signals by way of example, but the gain could be set in a similar manner with square waves as well.

Figure 12:
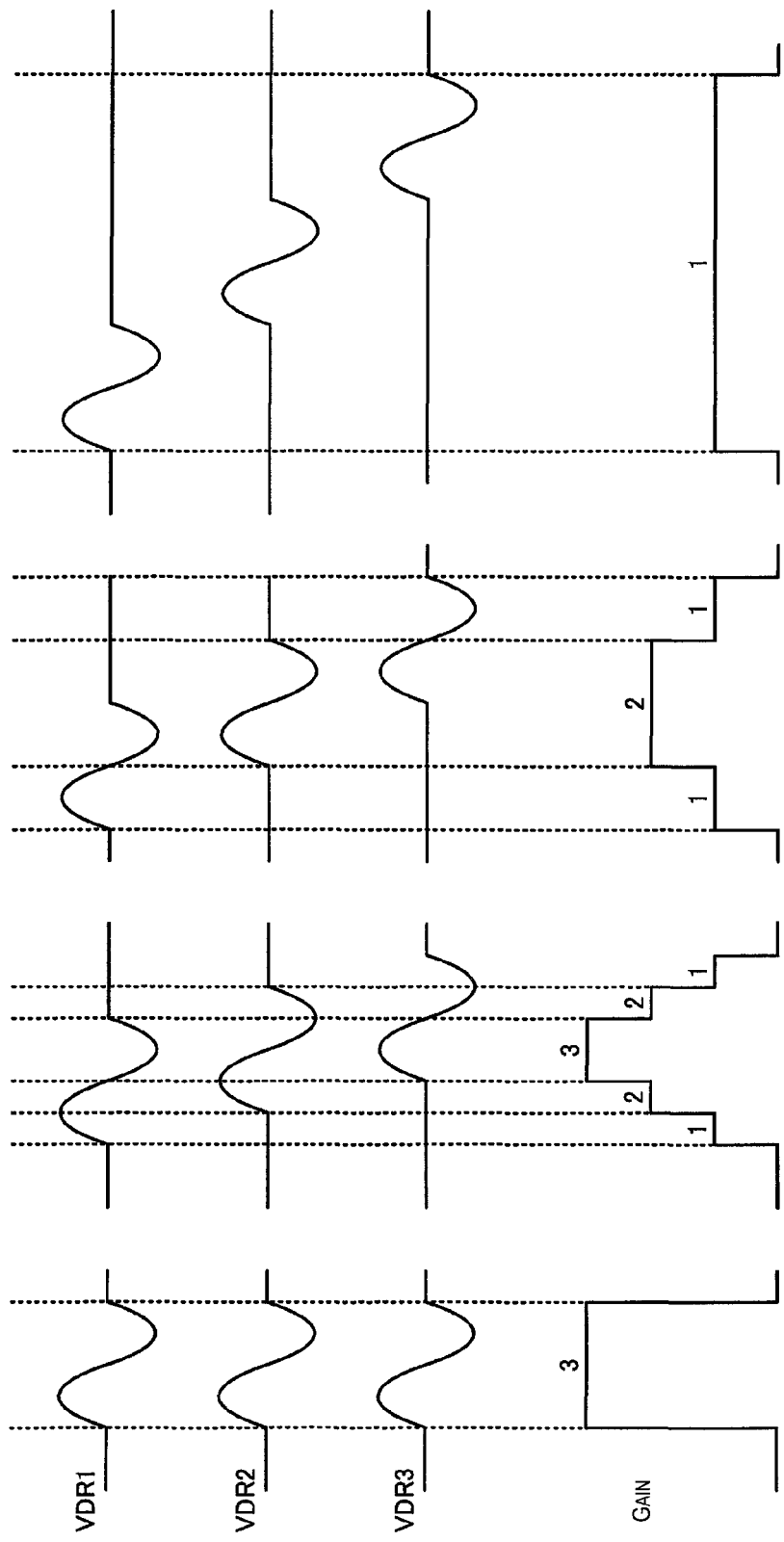
FIGS. 12A to 12D are a first example for a gain control.

FIG. 12A illustrates the case of the frontal emission mode; the phase difference between each of the drive signals for the first through third drive signals VDR1 to VDR3 is 0°. In such a case, the overlapping degree of the drive signals is 3, and the voltage fluctuations of the common electrode line are the largest, and thus the control unit 220 sets the gain to 3.

FIG. 12B illustrates the case of the phase scanning mode. The phase difference between each of the drive signals for the first through third drive signals VDR1 to VDR3 is 90°. In such a case, the steering angle is small and therefore the overlapping degree of the drive signals changes over time to 1, 2, 3, 2, and 1. In correspondence therewith, the control unit 220 causes the gain to change over time to 1, 2, 3, 2, and 1. That is, in a case where the first drive signal VDR1 is outputted at a first timing tb1 and the third drive signal VDR3 (more broadly, the n-th drive signal VDRn) is outputted at a third timing tb3 (more broadly, an n-th timing tbn), then the gain of the gain amplifiers G_AMP1 to G_AMPn is increased from the first timing tb1 toward a timing tbm intermediate between the first timing tb1 and the third timing tb3. The gain is then reduced from the intermediate timing tbm toward the third timing tb3. So doing causes the voltage amplitude of the first through third drive signals VDR1 to VDR3 to increase from the first timing tb1 toward the intermediate timing tbm, and to decrease from the intermediate timing tbm toward the third timing tb3.

FIG. 12C is also of the case of the phase scanning mode, but the steering angle is greater than that of the case of FIG. 12B. The phase difference between each of the drive signals for the first through third drive signals VDR1 to VDR3 is 180°. In such a case, the overlapping degree of the drive signals changes over time to 1, 2, and 1. In correspondence therewith, the control unit 220 causes the gain to change over time to 1, 2, and 1. That is, in a case where the first drive signal VDR1 is outputted at a first timing tc1 and the third drive signal VDR3 (more broadly, the n-th drive signal VDRn) is outputted at a third timing tc3 (more broadly, an n-th timing tcn), then the gain of the gain amplifiers G_AMP1 to G_AMPn is increased from the first timing tc1 toward a timing tcm intermediate between the first timing tc1 and the third timing tc3. The gain is then reduced from the intermediate timing tcm toward the third timing tc3. So doing causes the voltage amplitude of the first through third drive signals VDR1 to VDR3 to increase from the first timing tc1 toward the intermediate timing tcm, and to decrease from the intermediate timing tcm toward the third timing tc3.

FIG. 12D is also of the case of the phase scanning mode, but the steering angle is even greater than that of the case of FIG. 12C. The phase difference between each of the drive signals for the first through third drive signals VDR1 to VDR3 is 360°. In such a case, the overlapping degree of the drive signals is 1, and thus the control unit 220 sets the gain to 1.

As will be understood from FIGS. 12B and 12C, in a case where the phase difference between each of the drive signals is 90°, the maximum gain is 3, and in a case where the phase difference between each of the drive signals is 180°, the maximum gain is 2. As such, in a case where the phase difference between each of the drive signals is 90° (more broadly, is the first phase difference), the transmission circuit 210 outputs drive signals of a greater voltage amplitude than a case where the phase difference between each of the drive signals is 180° (more broadly, is the second phase difference), which is greater than the first phase difference. The same is also true of FIGS. 12B and 12D, and of FIGS. 12C and 12D.

It would still be possible to carry out a similar control with a configuration in which the voltage selection circuits V_SEL1 to V_SELn are used instead of the gain amplifiers G_AMP1 to G_AMPn. Instead of the gain control illustrated in FIGS. 12A to 12D, the control unit 220 could carry out a control in which, for example, a first, second, or third selection voltage is selected. In this case, the selection voltage of the voltage selection circuits V_SEL1 to V_SELn increases from the first timing toward the timing intermediate between the first timing and the n-th timing. The gain is then reduced from the intermediate timing toward the third timing.

FIGS. 13A to 13D illustrate a second example of the gain control by the control unit 220. The description herein relates to the first through third drive signals VDR1 to VDR3, for the sake of simplicity. FIGS. 13A to 13D illustrate sinusoidal drive signals by way of example, but the same also applies to square waves.

In the second example, the control unit 220 can control the gain by taking into account not only the overlapping degree of the drive signals but also the phase. More specifically, in a case where the three signals are in the same phase and overlap, the gain will be set to a maximum 4; in a case where two signals are in the same phase and overlap, the gain will be set to 3; in a case where three signals overlap but two of the signals are of inverse phase, the gain will be set to 2; in a case where the signals do not overlap, the gain will be set to 2; and in a case where two signals of inverse phase overlap, the gain will be set to 1. So doing makes it possible to carry out a control gain that takes into consideration the fact that overlapping of drive signals at inverse phase has a cancellation effect.

Figure 13:
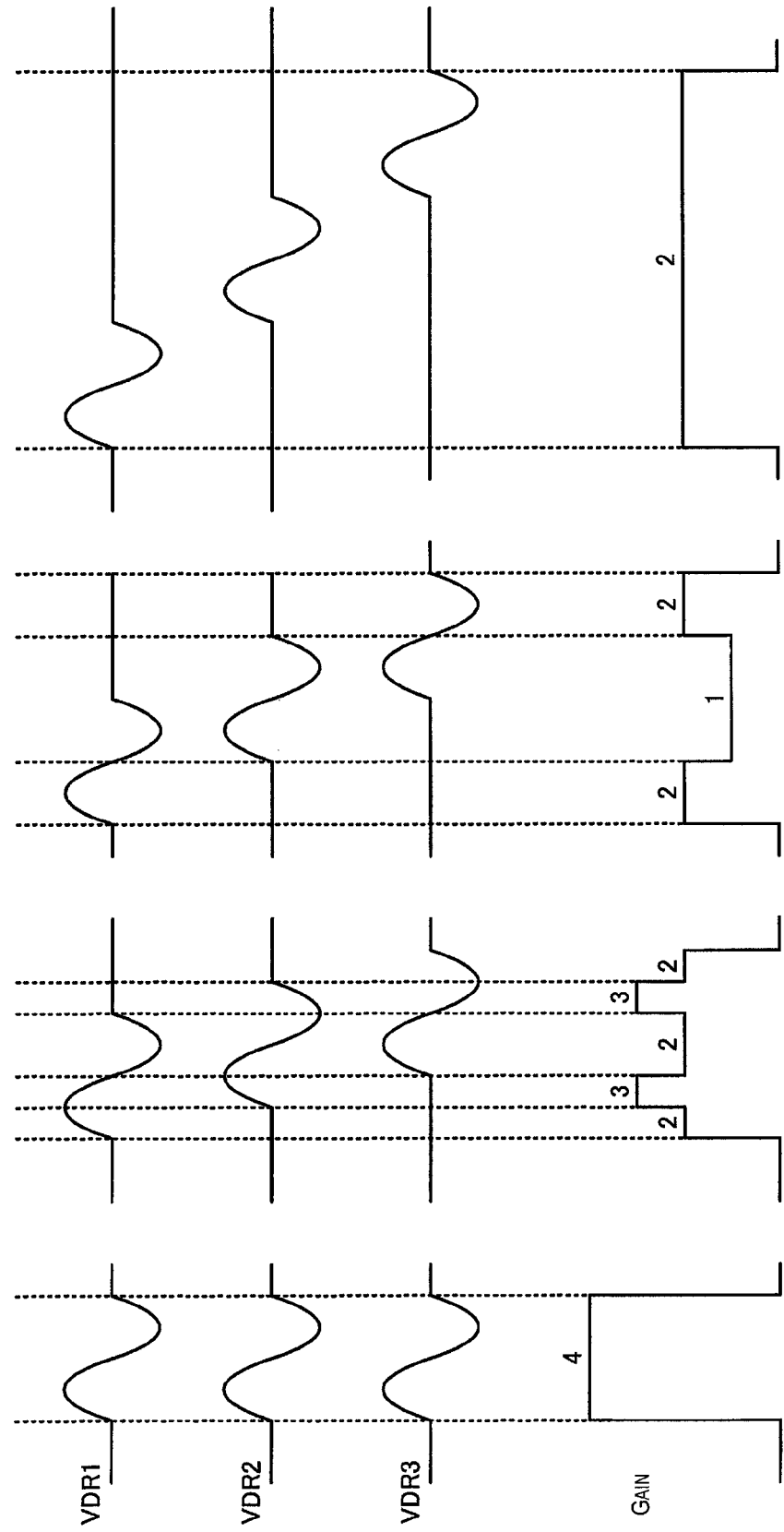
FIGS. 13A to 13D are a second example for a gain control.

FIG. 13A illustrates the case of the frontal emission mode. In such a case, three signals are of the same phase and overlap, and the voltage fluctuations in the common voltage line are the greatest, and thus the control unit 220 sets the gain to the maximum gain 4.

FIG. 13B illustrates the case of the phase scanning mode. In such a case, the control unit 220 causes the gain to change over time to 2, 3, 2, 3, and 2.

FIG. 13C also is the case of the phase scanning mode, but the steering angle is greater than the case in FIG. 13B. In such a case, the control unit 220 causes the gain to change over time to 2, 1, and 2.

FIG. 13D also is the case of the phase scanning mode, but the steering angle is even greater than the case in FIG. 13C. In such a case, the control unit 220 sets the gain to 2.

In a configuration in which the voltage selection circuits V_SEL1 to V_SELn are used instead of the gain amplifiers G_AMP1 to G_AMPn, then carrying out a control in which, for example, one from among the first through fourth selection voltages is selected instead of the gain control would still make it possible to carry out a similar control.

As described above, according to the drive apparatus 200 of the present embodiment, it is possible to control the voltage amplitude of the drive signals in accordance with the phase difference (time difference) of the drive signals. So doing makes it possible to reduce changes in the ultrasonic intensity corresponding to the steering angle, or alternatively to have a substantially constant ultrasonic wave intensity, during the phase scanning mode. Also, it is possible to increase the voltage amplitude of the drive signals in the case of the frontal emission mode, and thus it is possible to reduce the difference in ultrasonic wave intensity between the case of the frontal emission mode and the case of the phase scanning mode. As a result, it is possible to reduce changes in intensity imparted by the beam direction of the ultrasonic waves, and thus a highly accurate echo image can be obtained.

4. Ultrasonic Probe and Ultrasonic Diagnostic Apparatus

Figure 14:
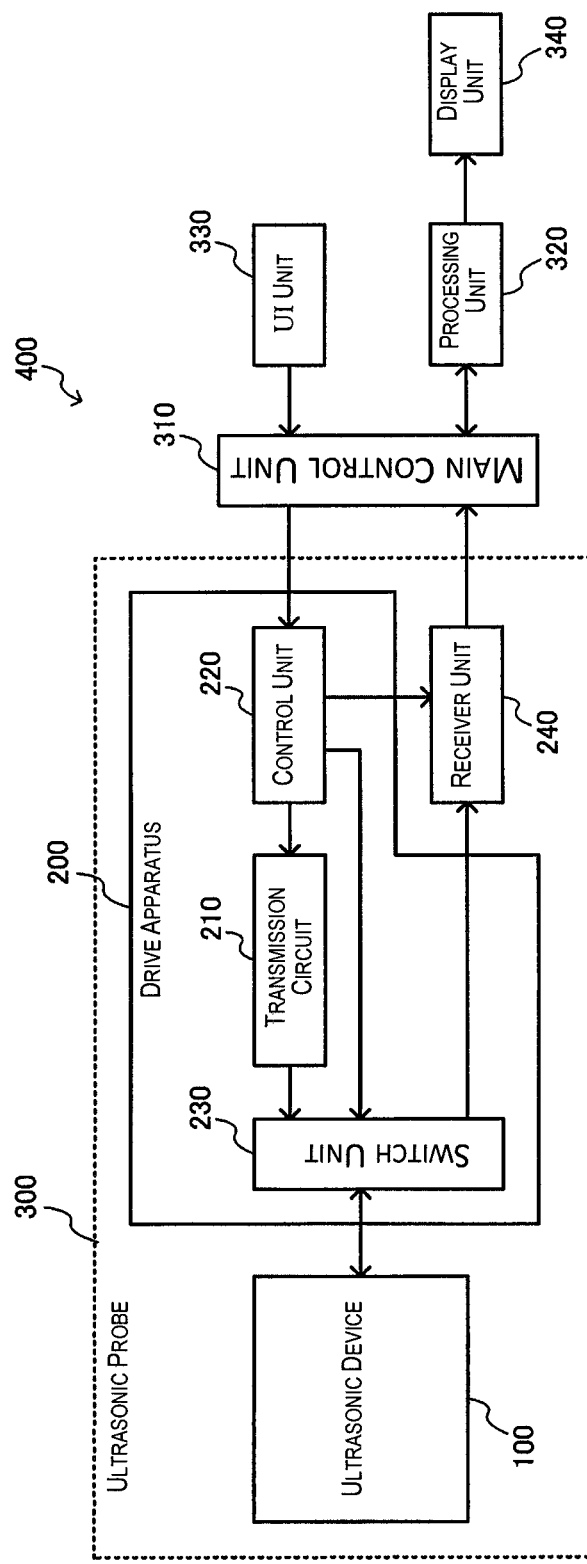
FIG. 14 is an example of a basic configuration for an ultrasonic probe and an ultrasonic diagnostic apparatus.

FIG. 14 illustrates a basic configuration example of an ultrasonic probe 300 and ultrasonic diagnostic apparatus 400 of the present embodiment. The ultrasonic probe 300 includes the ultrasonic device 100, the drive apparatus 200, and the receiver unit 240.

The receiver unit (an analog front end) 240 amplifies received signals, sets the gain, sets the frequency, carries out A/D conversion (analog/digital conversion), and so forth, and sends output to a processing unit 320 as detection data (detection information). The receiver unit 240 can be constituted of, for example, a low-noise amplifier, voltage controlled attenuator, programmable gain amplifier, low-pass filter, A/D converter, and the like.

The control unit controls the transmission circuit 210 and the switch unit 230 in the same manner as described above, and also controls the receiver unit 240 such as by setting the frequency of received signals and controlling the gain. The control unit 220 can be implemented with, for example, a field-programmable gate array (FPGA).

The control carried out by the control unit 220 can also be partially carried out by a main control unit 310 of the ultrasonic diagnostic apparatus 400.

The ultrasonic diagnostic apparatus 400 includes the ultrasonic probe 300, the main control unit 310, the processing unit 320, a user interface (UI) unit 330, and a display unit 340.

The main control unit 310 controls the ultrasonic probe 300 by controlling the transmission and receipt of ultrasonic waves, and controls the processing unit 320 by controlling image processing of detection data and the like. The processing unit 320 receives the detection data coming from the receiver unit 240 and carries out the necessary image processing, generates image data for display, and so forth. The UI unit 330 outputs a required instruction (command) to the main control unit 310 on the basis of an operation carried out by the user (for example, a touch panel operation or the like). The display unit 340 is, for example, a liquid crystal display or the like, and displays image data for display coming from the processing unit 320. The control carried out by the main control unit 310 can also be partially carried out by the control unit 220 of the drive apparatus 200.

Figure 15A:
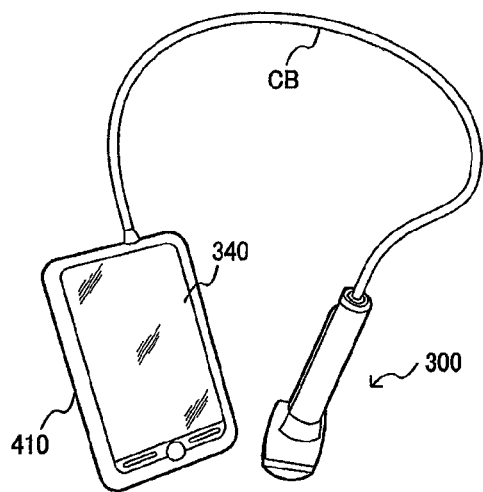
FIGS. 15A and 15B are an example of a specific configuration for an ultrasonic diagnostic device.
Figure 15B:
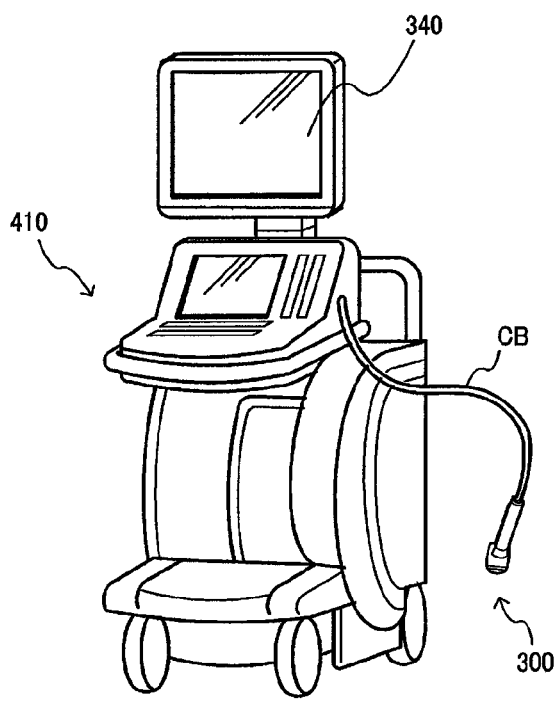

FIGS. 15A and 15B illustrates a specific configuration example for the ultrasonic diagnostic apparatus 400 of the present embodiment. FIG. 15A illustrates a portable ultrasonic diagnostic apparatus 400, and FIG. 15B illustrates a stationary ultrasonic diagnostic apparatus 400.

Both the portable and stationary ultrasonic diagnostic apparatuses 400 include the ultrasonic probe 300, a cable CB, and an ultrasonic diagnostic apparatus body 410. The ultrasonic probe 300 is connected to the ultrasonic diagnostic apparatus body 410 by the cable CB. The ultrasonic diagnostic apparatus body 410 includes the display unit 340 for displaying the image data for display.

Figure 15C:
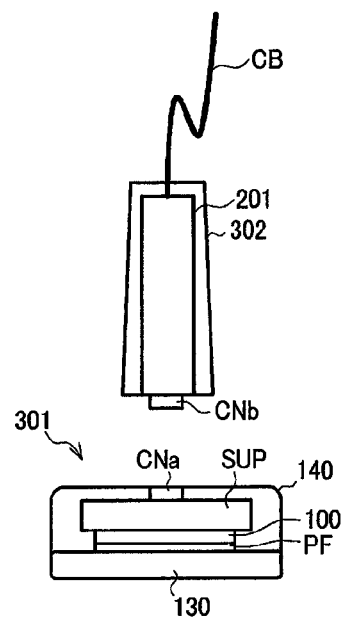
FIG. 15C is an example of a specific configuration for an ultrasonic probe.

FIG. 15C illustrates a specific configuration example for the ultrasonic probe 300 of the present embodiment. The ultrasonic probe 300 includes a probe head 301 and a probe body 302; as illustrated in FIG. 13C, the probe head 301 is detachable from the probe body 302.

The probe head 301 includes the ultrasonic device 100, a support member SUP, a contact member 130 for making contact with a subject, a protective member (protective film) PF for protecting the ultrasonic device 100, a connector CNa, and a probe housing 140. The ultrasonic device 100 is provided between the contact member 130 and the support member SUP.

The probe body 302 includes a processing device 201, and a probe body-side connector CNb. The processing device 201 includes the drive apparatus 200 and the receiver unit 240. The probe body-side connector CNb is connected to the probe head-side connector CNa. The probe body 302 is connected to the ultrasonic diagnostic apparatus body by the cable CB.

Though an embodiment has been described in greater detail above, it shall be readily understood by a person skilled in the art that there are numerous possible modifications which do not substantially depart from the novel matter and effects of the invention. As such, the modification examples of such description are understood to all also be included in the scope of the invention. For example, in the specification or accompanying drawings, a phrase mentioned at least once together with a different phrase of broader or similar meaning can also be replaced with the difference phrase in any portion in the specification or accompanying drawings. The configurations and operations of the drive apparatus, the ultrasonic probe, and the ultrasonic diagnostic apparatus are not limited to being what is described in the present embodiment, but rather a variety of modifications can be implemented.

What is claimed is:

1. A drive apparatus for an ultrasonic device, the drive apparatus, comprising:
   a transmission circuit configured to output a first drive signal to n-th (where n is an integer 2 or greater) drive signal to a first driving electrode line to n-th driving electrode line belonging to the ultrasonic device; and
   a controller configured to control the transmission circuit, wherein:

in a case where a phase difference between an i-th (where i is an integer 1≤i≤n−1) drive signal to i+1-th drive signal from among the first drive signal to n-th drive signal is a first phase difference, the transmission circuit outputs the first drive signal to n-th drive signal at a greater voltage amplitude than a case where the phase difference between the i-th drive signal and the i+1-th drive signal is a second phase difference greater than the first phase difference.

2. The drive apparatus as set forth in claim 1, wherein the transmission circuit outputs the first drive signal to n-th drive signal at a greater voltage amplitude in a case of a frontal emission mode than a case of a phase scanning mode.

3. The drive apparatus as set forth in claim 1, wherein the transmission circuit has a gain amplifier for which gain is controlled by the controller, and the controller controls voltage amplitude of the first drive signal to n-th drive signal by controlling the gain of the gain amplifier.

4. The drive apparatus as set forth in claim 3, wherein the transmission circuit further includes:

a signal generation circuit; and a delay circuit for which delay time is controlled by the controller, wherein:

the gain amplifier amplifies a reference signal coming from the signal generation circuit, and the delay circuit generates the first drive signal to n-th drive signal having a phase difference between the i-th drive signal and the i+1-th drive signal by delaying the amplified reference signal on the basis of control of the controller.

5. The drive apparatus as set forth in claim 3, wherein in a case where the first drive signal is outputted at a first timing and the n-th drive signal is outputted at an n-th timing, the gain of the gain amplifier increases from the first timing toward a timing intermediate between the first timing and the n-th timing and decreases from the intermediate timing toward the n-th timing, whereby the voltage amplitude of the first drive signal to the n-th drive signal increases from the first timing toward the intermediate timing, and decreases from the intermediate timing toward the n-th timing.

6. The drive apparatus as set forth in claim 5, wherein In the case where the first drive signal is outputted at the first timing and the n-th drive signal is outputted at the n-th timing, a selection voltage of a voltage selection circuit increases from the first timing toward the timing intermediate between the first timing and the n-th timing and decreases from the intermediate timing toward the n-th timing, whereby the voltage amplitude of the first drive signal to n-th drive signal increases from the first timing toward the intermediate timing and decreases from the intermediate timing toward the n-th timing.

7. The drive apparatus as set forth in claim 1, wherein the transmission circuit has a voltage selection circuit configured to select one from among a plurality of voltages to serve as a selection voltage, wherein:

the voltage selection circuit outputs a signal for which the voltage amplitude is the selected selection voltage, the controller controls voltage amplitude of the signal for which the voltage amplitude is the selection voltage by carrying out a control in which the selection voltage is switched, and the transmission circuit outputs the first drive signal to n-th drive signal on the basis of the signal for which the voltage amplitude is the selection voltage.

8. The drive apparatus as set forth in claim 7, wherein the transmission circuit further includes:

a signal generation circuit; and a delay circuit for which delay time is controlled by the controller, wherein the voltage selection circuit outputs the signal for which voltage amplitude is the selection voltage in synchronization with a reference signal coming from the signal generation circuit, the delay circuit delays the signal for which the voltage amplitude is the selection voltage coming from the voltage selection circuit on the basis of control of the controller, and the transmission circuit outputs the first drive signal to n-th drive signal having a phase difference between the i-th drive signal and the i+1-th drive signal on the basis of the delayed signal coming from the delay circuit.

9. The drive apparatus as set forth in claim 1, further comprising:

a common voltage monitoring circuit configured to monitor a voltage of a common electrode line belonging to the ultrasonic device, wherein the controller controls voltage amplitude of the first drive signal to n-th drive signal on the basis of a monitoring result from the common voltage monitoring circuit.

10. The drive apparatus as set forth in claim 9, wherein the controller carries out a control in which a greater amplitude of voltage of the common electrode line correlates to increasing the voltage amplitude of the first drive signal to n-th drive signal on the basis of the monitoring result from the common voltage monitoring circuit.

11. The drive apparatus as set forth in claim 1, wherein the first drive signal to n-th drive signal are m (where m is a natural multiple of 0.5) sinusoidal waves or square waves.

12. An ultrasonic probe, characterized by comprising the drive apparatus as set forth in claim 1.

13. An ultrasonic diagnostic apparatus, comprising:

the drive apparatus as set forth in claim 1; and a display configured to display image data for display generated on the basis of a received signal coming from the ultrasonic device.

14. A drive apparatus for an ultrasonic device, the drive apparatus being characterized by comprising:

a transmission circuit configured to output a first pulse signal to n-th (where n is an integer 2 or greater) pulse signal outputted to a first driving electrode line to n-th driving electrode line belonging to the ultrasonic device; and a controller configured to control the transmission circuit, wherein:

the transmission circuit, in a first mode outputs at an identical timing an i-th (where i is an integer 1≤i≤n−1) pulse signal to i+1-th pulse signal from among the first pulse signal to n-th pulse signal, and in a second mode outputs the i+1-th pulse signal at a timing that is delayed from the timing at which the i-th pulse signal is outputted, and in the first mode outputs the first pulse signal to n-th pulse signal at a greater pulse signal voltage amplitude than in the second mode.

15. A drive apparatus for an ultrasonic device in which a first ultrasonic element to n-th (where n is an integer 2 or greater) ultrasonic element provided with a piezoelectric element in which a piezoelectric body is arranged between two electrodes are arranged in a rectilinear fashion, the drive apparatus being characterized by comprising:

a transmission circuit configured to output a first drive signal to n-th drive signal to a first driving electrode line to n-th driving electrode line connected to either of the two electrodes of each of the first ultrasonic element to n-th ultrasonic element; and a controller configured to control the transmission circuit, wherein:

in a case where there is no phase difference between an i-th (where i is an integer $1 \leq i \leq n-1$) drive signal and an i+1-th drive signal from among the first drive signal to n-th drive signal, the transmission circuit outputs a drive signal of a greater voltage amplitude than the voltage amplitude of a drive signal of a case where a phase difference between the i-th drive signal and the i+1-th drive signal is in a range 90° to 180°.

* * * * *